United States Patent
Kiyono et al.

(10) Patent No.: US 10,292,962 B2
(45) Date of Patent: May 21, 2019

(54) PHARMACEUTICAL COMBINATION COMPRISING METFORMIN AND DIHYDROQUERCETIN AND ITS USE FOR THE TREATMENT OF CANCER

(71) Applicant: RESEARCH INSTITUTE FOR NUTRITION AND AGING CO., LTD., Saitama-pre (JP)

(72) Inventors: Kunihiko Kiyono, Osaka (JP); Kenji Onishi, Osaka (JP); Yasuharu Nagahama, Osaka (JP); Takashi Watanabe, Osaka (JP)

(73) Assignee: RESEARCH INSTITUTE FOR NUTRITION AND AGING CO., LTD., Saitama-Pre (JP)

( * ) Notice: Subject to any disclaimer, the term of this patent is extended or adjusted under 35 U.S.C. 154(b) by 0 days.

(21) Appl. No.: 15/723,369

(22) Filed: Oct. 3, 2017

(65) Prior Publication Data
US 2018/0050014 A1 Feb. 22, 2018

Related U.S. Application Data

(62) Division of application No. 14/893,127, filed as application No. PCT/JP2014/064354 on May 23, 2014, now Pat. No. 9,808,440.

(30) Foreign Application Priority Data

May 24, 2013 (JP) .................. 110278/2013

(51) Int. Cl.
*A61K 31/353* (2006.01)
*A61K 31/155* (2006.01)
*A61K 45/06* (2006.01)

(52) U.S. Cl.
CPC .......... *A61K 31/353* (2013.01); *A61K 31/155* (2013.01); *A61K 45/06* (2013.01)

(58) Field of Classification Search
CPC ..................... A61K 31/155; A61K 31/353
See application file for complete search history.

(56) References Cited

U.S. PATENT DOCUMENTS

| 8,058,243 B2 | 11/2011 | Tyers et al. |
| 2007/0036834 A1 | 2/2007 | Pauletti et al. |
| 2012/0220664 A1 | 8/2012 | Struhl |

FOREIGN PATENT DOCUMENTS

| JP | 6-247851 | 6/1994 |
| WO | WO 2009/153009 | 12/2009 |
| WO | WO 2010/042886 | 4/2010 |
| WO | WO 2012/122295 | 9/2012 |
| WO | WO 2012/166008 | 12/2012 |

OTHER PUBLICATIONS

Tang Xiping et al., *China Oncology*, vol. 22, No. 11, pp. 801-807 (2012).
Niu Zhuang et al., *Chinese Journal of Laboratory Diagnosis*, vol. 11, No. 10, pp. 1346-1348 (2007).
Doi et al., *Cancer Sci.*, 2010, vol. 101. No. 6, pp. 1529-1535.
Verma et al., *Journal of Applied Pharmaceutical Science*, vol. 2, No. 1, pp. 41-46 (2012).
Li et al., *Mol. Carcinog.*, 2012, vol. 51, No. 1, pp. 64-74.
Moridani et al., "Comparative quantitative structure toxicity relationships for flavonoids evaluated in isolated rat hepatocytes and HeLa tumor cells", *Chemico-Biological Interactions*, 139 (2002), pp. 251-264.
Nakajima et al., "Inhibition of colon carcinoma metastasis and gelatinase production by flavonoids", *Clinical & Experimental Metastasis*, vol. 12, No. 5, p. 68, Abstract 185 (1994).
Matsuo et al., "Hyperactivation of 4E-Binding Protein 1 as a Mediator of Biguanide-Induced Cytotoxicity during Glucose Deprivation", *Mol. Cancer Ther.*, 11(5), pp. 1082-1091 (2012).
Aruoma et al., "Neuroprotection by bioactive components in medicinal and food plant extracts", *Mutation Research*, 544, pp. 203-215 (2003).
Shen et al., "Structurally related antitumor effects of flavanones in vitro and in vivo: involvement of caspase 3 activation, p21 gene expression, and reactive oxygen species production", *Toxicology and Applied Pharmacology*, 197, pp. 84-95 (2004).
Stan et al., "Chemoprevention strategies for pancreatic cancer", *Nat Rev Gastroenterol Hepatol*, 7(6), pp. 347-356 (2010).
Feng et al., "The impact of type 2 diabetes and antidiabetic drugs on cancer cell growth", *J Cell Mol Med*, 15(4), pp. 825-836 (2011).
Zhou et al., "Dietary polyphenol quercetin targets pancreatic cancer stem cells", *International Journal of Oncology*, 37, pp. 551-561 (2010).
Woo et al., "Flavanones inhibit the clonogenicity of HCT116 cololectal cancer cells", *International Journal of Molecular Medicine*, 29, pp. 403-408 (2012).
Adikrisna et al., "Identification of Pancreatic Cancer Stem Cells and Selective Toxicity of Chemotherapeutic Agents", *Gastroenterology*, 143, pp. 234-245 (2012).
Schroeter et al., "Phenolic Antioxidants Attenuate Neuronal Cell Death Following Uptake of Oxidized Low-Density Lipoprotein", *Free Radical Biology & Medicine*, vol. 29, No. 12, pp. 1222-1233 (2000).
Pendry et al., "Phytochemical Evaluation of Selected Antioxidant-Containing Medicinal Plants for Use in the Preparation of a Herbal Formula—A Preliminary Study", *Chemistry & Biodiversity*, vol. 2, pp. 917-922 (2005).
Thomson Reuters Cortellis™, "Carboxymethylated-kappa-casein: A convenient tool for the identification of polyphenolic inhibitors of amyloid fibril formation" (2012), 6 page summary of article having the same title by Carver et al. in Bioorg. Med. Chem., (2010), 18, No. 1, 222-8.

(Continued)

*Primary Examiner* — Samira J Jean-Louis
(74) *Attorney, Agent, or Firm* — Finnegan, Henderson, Farabow, Garrett & Dunner LLP

(57) ABSTRACT

Provided is a novel medicament capable of reducing the side effects of metformin or a pharmaceutically acceptable salt thereof and useful as an anti-malignant tumor agent, in which metformin or a pharmaceutically acceptable salt thereof and dihydroquercetin or a pharmaceutically acceptable salt thereof are combined.

2 Claims, 4 Drawing Sheets

(56) References Cited

OTHER PUBLICATIONS

Itaya et al., "Effects of Taxifolin on the Serum Cholesterol Level in Rats", *Biosci. Biotech. Biochem.*, 56(9), pp. 1492-1494 (1992).

Lee et al., "The Chemopreventive Effect of Taxifolin is Exerted Through ARE-Dependent Gene Regulation", *Biol. Pharm. Bull.*, 30(6), pp. 1074-1079 (2007).

Aghdassi et al., "Heat Shock Protein 70 Increases Tumorigenicity and Inhibits Apoptosis in Pancreatic Adenocarcinoma," *Cancer Research*, 67, pp. 616-625 (2007).

Pantouris et al., "Antitumour agents as inhibitors of tryptophan 2,3-dioxygenase", *Biochemical and Biophysical Research Communications*, 443, pp. 28-31 (2014).

Li et al., "Chemical Constituents of Propolis from Myanmar and Their Preferential Cytotoxicity against a Human Pancreatic Cancer Cell Line", *J. Nat. Prod.*, 72, pp. 1283-1287 (2009).

Brusselmans et al., "Metabolism and Bioenergetics: Induction of Cancer Cell Apoptosis by Flavonoids is Associated with Their Ability to Inhibit Fatty Acid Synthase Activity", *The Journal of Biological Chemistry*, 280, pp. 5636-5645 (2005).

Lee et al., "Inhibitory effect of luteolin on hepatocyte growth factor/scatter factor-induced HepG2 cell invasion involving both MAPK/ERKs and PI3K-Akt pathways", *Chemico-Biological Interactions*, 160, pp. 123-133 (2006).

Uda et al., "Induction of the anticarcinogenic marker enzyme, quinone reductase, in murine hepatoma cells in vitro by flavonoids", *Cancer Letters*, 120, pp. 213-216 (1997).

Ding et al., "Lipoxygenase Inhibition Induced Apoptosis, Morphological Changes, and Carbonic Anhydrase Expression in Human Pancreatic Cancer Cells", *Biochemical and Biophysical Research Communications*, 266, pp. 392-399 (1999).

Oi et al., "Taxifolin suppresses UV-induced skin carcinogenesis by targeting EGFR and PI3-K", *Cancer Prev. Res.* (Phila). 2012, 5(9):1103-1114.

Kourelis et al., "Metformin and cancer: new applications for an old drug", *Med. Oncol.*, published online Feb. 8, 2011, DOI 10.1007/s12032-011-9846-7 (4 pages).

PHARMACEUTICAL COMBINATION COMPRISING METFORMIN AND DIHYDROQUERCETIN AND ITS USE FOR THE TREATMENT OF CANCER

This is a division of application Ser. No. 14/893,127, filed Nov. 23, 2015, which is a national stage entry under 35 U.S.C. § 371 of PCT/JP2014/064354, filed May 23, 2014, which claims priority to JP 2013-110278, filed May 24, 2013, all of which are incorporated herein by reference.

TECHNICAL FIELD OF THE INVENTION

The present invention relates to a medicament wherein metformin or a pharmaceutically acceptable salt thereof, and dihydroquercetin or a pharmaceutically acceptable salt thereof are combined.

BACKGROUND OF THE INVENTION

Patent document 1 describes a method for the treatment and prevention of metabolic disorders and other diseases by administering a pyrone analog, or a derivative thereof, in combination with one or more additional agents such as, for example, lipid lowering agents or glucose lowering agents. As one of the examples of the pyrone analog, taxifolin is described and, as one of the examples of the glucose lowering agent, metformin is described. However, this document does not disclose any specific example of a combination of metformin and taxifolin, and does not describe a synergistic effect against malignant tumors or a lactic acidosis-lowering effect of a medicament containing them in combination.

DOCUMENT LIST

Patent Document patent document 1: WO 2010/042886

SUMMARY OF THE INVENTION

Problems to be Solved by the Invention

Metformin hydrochloride is commercially available as a biguanide oral hypoglycemic agent, and is known to have an action to activate AMP-activated protein kinase (AMPK).

In recent years, it has been reported that a compound having an action to activate AMPK (AMPK activating agent) such as metformin, phenformin, oligomycin, dinitrophenol, 2-deoxyglucose, 5-aminoimidazole-4-carboxyamide ribonucleotide, hydrogen peroxide, sorbitol, calcimycin, 4-hydroxy-3-(2'-hydroxybiphenyl-4-yl)-6-oxo-6,7-dihydrothieno[2,3-b]pyridine-5-carbonitrile (A-769662), galegine, troglitazone, phenobarbital, quercetin, resveratrol, berberine and the like shows an anti-malignant tumor effect by a single use thereof or a combined use with existing anticancer agents, and the development thereof as an anti-malignant tumor agent has been considered.

However, of the above, AMPK activating agents such as metformin, phenformin, 5-aminoimidazole-4-carboxyamide ribonucleotide, sorbitol, calcimycin, A-769662, galegine, troglitazone and the like are associated with a problem of severe lactic acidosis in the patients who received the administration.

The present invention aims to provide a novel medicament capable of reducing the side effects of metformin or a pharmaceutically acceptable salt thereof and useful as an anti-malignant tumor agent.

Metformin is known to have an action to suppress cancer stem cells. Such medicament that suppresses cancer stem cells is expected to not only provide an anti-malignant tumor effect, but also enable prevention of cancer metastasis and prevention of recurrence.

The present invention also aims to provide a novel medicament having an action to suppress cancer stem cells and useful as an anti-malignant tumor agent.

Means of Solving the Problems

The present inventors have conducted intensive studies in an attempt to solve the aforementioned problems and found that a combination of metformin or a pharmaceutically acceptable salt thereof and dihydroquercetin or a pharmaceutically acceptable salt thereof suppresses an increase in the blood lactic acid value induced by metformin or a pharmaceutically acceptable salt thereof. In addition, the present inventors have found that a combination of metformin or a pharmaceutically acceptable salt thereof and dihydroquercetin or a pharmaceutically acceptable salt thereof remarkably potentiates the anti-malignant tumor action of metformin or a pharmaceutically acceptable salt thereof.

The present inventors have also found that dihydroquercetin or a pharmaceutically acceptable salt thereof is effective for the prophylaxis or treatment of pancreatic cancer.

The present inventors have found that dihydroquercetin or a pharmaceutically acceptable salt thereof is effective for suppressing pancreatic cancer stem cells.

Based on such finding, the present inventors have conducted further studies and completed the present invention.

Accordingly, the present invention provides the following.

[1] A medicament in which metformin or a pharmaceutically acceptable salt thereof, and dihydroquercetin or a pharmaceutically acceptable salt thereof are combined, wherein metformin or a pharmaceutically acceptable salt thereof, and dihydroquercetin or a pharmaceutically acceptable salt thereof are contained in a single preparation, or metformin or a pharmaceutically acceptable salt thereof, and dihydroquercetin or a pharmaceutically acceptable salt thereof are separately formulated into pharmaceutical compositions and used in combination.

[2] The medicament of the above-mentioned [1], wherein metformin or a pharmaceutically acceptable salt thereof, and dihydroquercetin or a pharmaceutically acceptable salt thereof are contained in a single preparation.

[3] The medicament of the above-mentioned [1], wherein metformin or a pharmaceutically acceptable salt thereof, and dihydroquercetin or a pharmaceutically acceptable salt thereof are separately formulated into pharmaceutical compositions and used in combination.

[4] The medicament of any of the above-mentioned [1] to [3] for the prophylaxis or treatment of a malignant tumor.

[5] The medicament of the above-mentioned [4], wherein the malignant tumor is childhood brain tumor selected from the group consisting of astroglioma, malignant medulloblastoma, germ cell tumor, craniopharyngioma and ependymoma; adult brain tumor selected from the group consisting of glioma, glial tumor, meningioma, pituitary adenoma and neurinoma; head and neck cancer selected from the group consisting of maxillary sinus cancer, pharyngeal cancer, laryngeal cancer, mouth cavity cancer, lip cancer, tongue cancer and parotid cancer; thoracic cancer and tumor selected from the group consisting of small cell lung cancer, non-small cell lung cancer, lung adenomatosis and mesothelioma; gastrointestinal cancer and tumor selected from the group consisting of esophagus cancer, liver cancer, primary liver cancer, gall bladder cancer, bile duct cancer, gastric cancer, colorectal cancer, colon cancer, rectal cancer, anal cancer, pancreatic cancer and pancreatic endocrine tumor; urinary organ cancer and tumor selected from the group consisting of penile cancer, renal pelvis ureteral cancer, renal cell cancer, testis tumor, prostate cancer, urinary bladder cancer, Wilms tumor and urothelial cancer; gynecological cancer and tumor selected from the group consisting of vulvar cancer, cervical cancer, uterine body cancer, endometrial cancer, uterus sarcoma, chorionic cancer, vagina cancer, breast cancer, ovarian cancer and ovarian germ, cell tumor; adult and childhood soft tissue sarcoma; bone tumor selected from the group consisting of osteosarcoma and Ewing's tumor; cancer and tumor of endocrine tissue selected from the group consisting of adrenal cortex cancer and thyroid cancer; malignant lymphoma and leukemia selected from the group consisting of malignant lymphoma, non-Hodgkin's lymphoma, Hodgkin's disease, multiple myeloma, plasma cell tumor, acute myeloid leukemia, acute lymphatic leukemia, adult T-cell leukemia lymphoma, chronic myeloid leukemia and chronic lymphatic leukemia; and skin cancer and tumor selected from the group consisting of chronic myeloproliferative disease, malignant melanoma, squamous cell cancer, basal cell cancer and mycosis fungoides.

[6] The medicament of any of the above-mentioned [1] to [5] for treating a patient, for whom an anti-malignant tumor drug other than metformin and a pharmaceutically acceptable salt thereof, and dihydroquercetin and a pharmaceutically acceptable salt thereof provides only an insufficient effect.

[7] The medicament of any of the above-mentioned [1] to [5], wherein one or more kinds of anti-malignant tumor drugs other than metformin and a pharmaceutically acceptable salt thereof, and dihydroquercetin and a pharmaceutically acceptable salt thereof are combined.

[8] The medicament of the above-mentioned [6] or [7], wherein the anti-malignant tumor drug other than metformin and a pharmaceutically acceptable salt thereof, and dihydroquercetin and a pharmaceutically acceptable salt thereof is a molecule target drug, alkylating agent, metabolic antagonist, plant alkaloid, anticancer antibiotic, hormone agent or immunotherapeutic agent.

[9] A commercial package comprising the medicament of any of the above-mentioned [1] to [8] and a written matter associated therewith, the written matter stating that the medicament can or should be used for the prophylaxis or treatment of a malignant tumor.

[10] An agent for reducing the side effect of metformin or a pharmaceutically acceptable salt thereof, which comprises dihydroquercetin or a pharmaceutically acceptable salt thereof as an active ingredient.

[11] An enhancer of an anti-malignant tumor action of metformin or a pharmaceutically acceptable salt thereof, which comprises dihydroquercetin or a pharmaceutically acceptable salt thereof as an active ingredient.

[12] An agent for reducing the side effect of metformin or a pharmaceutically acceptable salt thereof comprising dihydroquercetin or a pharmaceutically acceptable salt thereof as an active ingredient, which is used in combination with metformin or a pharmaceutically acceptable salt thereof.

[13] An enhancer of an anti-malignant tumor action comprising dihydroquercetin or a pharmaceutically acceptable salt thereof as an active ingredient, which is used in combination with metformin or a pharmaceutically acceptable salt thereof.

[14] Use of dihydroquercetin or a pharmaceutically acceptable salt thereof in combination with metformin or a pharmaceutically acceptable salt thereof in the production of a medicament for the prophylaxis or treatment of a malignant tumor.

[15] A method for the prophylaxis or treatment of a malignant tumor, comprising administering metformin or a pharmaceutically acceptable salt thereof, and dihydroquercetin or a pharmaceutically acceptable salt thereof to a subject in need thereof, wherein metformin or a pharmaceutically acceptable salt thereof, and dihydroquercetin or a pharmaceutically acceptable salt thereof are administered as a single preparation or separate preparations which are administered simultaneously or at different time points.

[16] A medicament for the prophylaxis or treatment of pancreatic cancer, comprising dihydroquercetin or a pharmaceutically acceptable salt thereof as an active ingredient.

[17] A method for the prophylaxis or treatment of pancreatic cancer, comprising administering dihydroquercetin or a pharmaceutically acceptable salt thereof to a subject in need thereof.

[18] Use of dihydroquercetin or a pharmaceutically acceptable salt thereof as a medicament for the prophylaxis or treatment of pancreatic cancer.

[19] Dihydroquercetin or a pharmaceutically acceptable salt thereof for use in the prophylaxis or treatment of pancreatic cancer.

[20] Use of dihydroquercetin or a pharmaceutically acceptable salt thereof in the production of a medicament for the prophylaxis or treatment of pancreatic cancer.

[21] A pancreatic cancer stem cell inhibitor comprising dihydroquercetin or a pharmaceutically acceptable salt thereof as an active ingredient.

[22] A method of suppressing a pancreatic cancer stem cell, comprising administering dihydroquercetin or a pharmaceutically acceptable salt thereof to a subject in need thereof.

[23] Use of dihydroquercetin or a pharmaceutically acceptable salt thereof as a pancreatic cancer stem cell inhibitor.

[24] Dihydroquercetin or a pharmaceutically acceptable salt thereof for use in suppressing a pancreatic cancer stem cell.

[25] Use of dihydroquercetin or a pharmaceutically acceptable salt thereof in producing a pancreatic cancer stem cell inhibitor.

[26] A medicament comprising metformin or a pharmaceutically acceptable salt thereof for use in combination with dihydroquercetin or a pharmaceutically acceptable salt thereof.

[27] A medicament comprising dihydroquercetin or a pharmaceutically acceptable salt thereof for use in combination with metformin or a pharmaceutically acceptable salt thereof.

Effect of the Invention

The medicament of the present invention containing metformin or a pharmaceutically acceptable salt thereof and dihydroquercetin or a pharmaceutically acceptable salt thereof in combination has a synergistic anti-malignant tumor effect and is useful as an anti-malignant tumor drug.

The medicament of the present invention is a safe medicament that reduces lactic acidosis, since dihydroquercetin or a pharmaceutically acceptable salt thereof suppresses an increase in the blood lactic acid value induced by metformin or a pharmaceutically acceptable salt thereof.

Since the medicament of the present invention has a synergistic anti-malignant tumor effect, it enables low dosing, and further, is expected to reduce side effects.

The medicament of the present invention containing dihydroquercetin or a pharmaceutically acceptable salt thereof as an active ingredient is useful as a prophylactic or therapeutic drug for pancreatic cancer.

Gemcitabine which is a drug of first alternative for the treatment of pancreatic cancer permits growth of pancreatic cancer stem cells, as shown in the results of the below-mentioned Example 12.

The medicament of the present invention having a synergistic pancreatic cancer stem cell suppressive effect is particularly useful as a prophylactic or therapeutic drug for pancreatic cancer. In addition, the combination of the medicament of the present invention and gemcitabine is expected to improve clinical problems of an increase of cancer stem cells and an increase of recurrence risk in the gemcitabine treatment, and is particularly useful as a prophylactic or therapeutic drug for pancreatic cancer.

The medicament of the present invention, containing dihydroquercetin or a pharmaceutically acceptable salt thereof as an active ingredient, shows a pancreatic cancer stem cell suppressive effect. Therefore, it is useful as a prophylactic or therapeutic drug for pancreatic cancer, and further expected to prevent metastasis or recurrence of pancreatic cancer.

Figure 1:
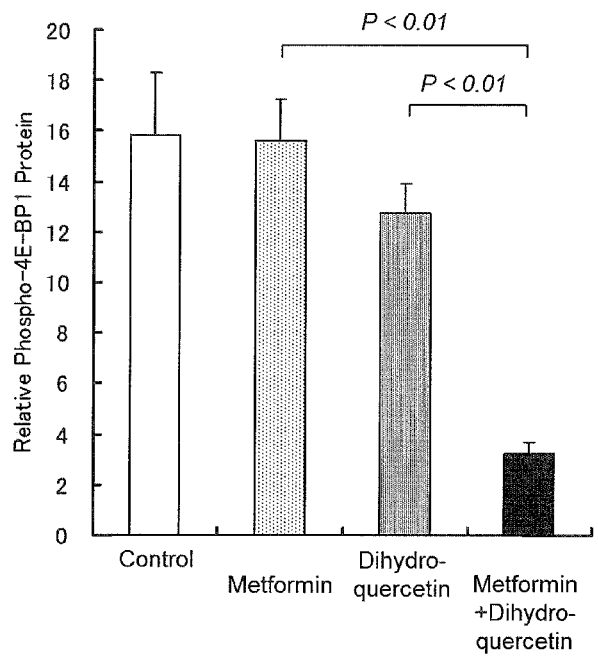
FIG. 1 shows the results of Example 1.

DESCRIPTION OF EMBODIMENTS (I) Combined Use of Metformin or a Pharmaceutically Acceptable Salt Thereof and Dihydroquercetin or a Pharmaceutically Acceptable Salt Thereof Examples of the pharmaceutically acceptable salt of metformin include salt with inorganic acid, salt with organic acid, salt with acidic amino acid and the like.

Examples of the salt with inorganic acid include a salt with hydrochloric acid, hydrobromic acid, nitric acid, sulfuric acid, phosphoric acid and the like. Examples of the salt with organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Examples of the salt with acidic amino acid include a salt with aspartic acid, glutamic acid and the like. Of these, hydrochloride is preferable.

Dihydroquercetin is a compound wherein the double bond between the 2-position and the 3-position of the pyran ring of quercetin has been reduced, and is represented by the following formula:

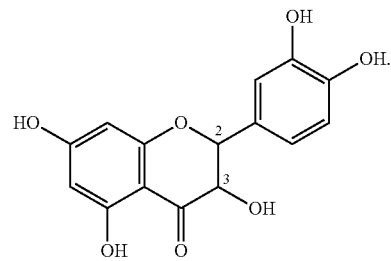 [SMILES: O=C1c2c(O)cc(O)cc2OC(c2ccc(O)c(O)c2)C1O]

Dihydroquercetin contains 4 stereoisomers based 2 asymmetric carbon atoms (2-position and 3-position of chromane ring) ((2R,3R)-dihydroquercetin, (2S,3S)-dihydroquercetin, (2R,3S)-dihydroquercetin, (2S,3R)-dihydroquercetin). While dihydroquercetin in the present invention may be a combination of one or more kinds of these isomers or a racemate of these (e.g., mixture of (2R,3R)-dihydroquercetin and (2S,3S)-dihydroquercetin), the racemate of (2R,3R)-dihydroquercetin and (2S,3S)-dihydroquercetin, and (2R,3R)-dihydroquercetin, are preferable, and (2R,3R)-dihydroquercetin is particularly preferable.

Of the isomers, it is known that (2R,3R)-dihydroquercetin represented by the following formula:

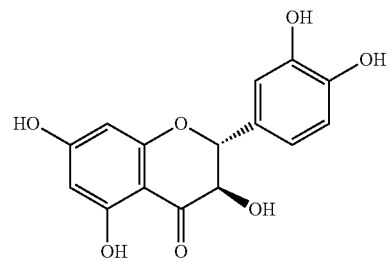 [SMILES: O=C1c2c(O)cc(O)cc2O[C@H](c2ccc(O)c(O)c2)[C@H]1O]

is contained in *Larix sibirica*, and is also called taxifolin. In the present invention, naturally-occurring substances such as taxifolin extracted by a known method and the like may also be used, and commercially available products can also be used.

Examples of the pharmaceutically acceptable salt of dihydroquercetin include salt with inorganic base, salt with organic base, salt with basic amino acid and the like.

Examples of the salt with inorganic base include a salt with alkali metal such as sodium, potassium and the like, alkaline earth metal such as calcium, magnesium and the like, and aluminum, ammonium and the like. Examples of the salt with organic base include a salt with trimethylamine, triethylamine, pyridine, picoline, ethanolamine, diethanolamine, triethanolamine, dicyclohexylamine, N,N-dibenzylethylenediamine and the like. Examples of the salt with basic amino acid include a salt with arginine, lysine, ornithine and the like. Examples of a preferable salt include alkali metal salt and alkaline earth metal salt.

The metformin and a pharmaceutically acceptable salt thereof, and dihydroquercetin and a pharmaceutically acceptable salt thereof usable in the present invention also encompass the same isotope labeled compounds wherein one or more atoms are replaced by one or more atoms having particular atom mass or mass number. Examples of the isotope that can be incorporated into these compounds include hydrogen, carbon, nitrogen, oxygen, sulfur, fluorine, and chlorine isotope such as $^2$H, $^3$H, $^{13}$C, $^{14}$C, $^{15}$N, $^{18}$O, $^{17}$O, $^{33}$S, $^{34}$S, $^{36}$S, $^{18}$F, $^{36}$Cl and the like. A particular isotope-labeled compound containing the above-mentioned isotope and/or other isotope of other atom, for example, a compound incorporating a radioactive isotope such as $^3$H, $^{14}$C and the like is useful for drug tissue distribution assay and/or substrate tissue distribution assay. A tritiated (i.e., $^3$H) isotope and carbon-14 (i.e., $^{14}$C) isotope are particularly preferred in view of the easiness of preparation and detectability. Furthermore, substitution with a heavier isotope such as deuterium (i.e., $^2$H) and the like is expected to improve metabolic stability, for example, by affording particular advantages in the treatment due to an increase in the in vivo half-life or a decrease in the necessary dose.

In the medicament of the present invention, metformin or a pharmaceutically acceptable salt thereof and dihydroquercetin or a pharmaceutically acceptable salt thereof are used in combination. In the medicament of the present invention, metformin or a pharmaceutically acceptable salt thereof, and dihydroquercetin or a pharmaceutically acceptable salt thereof may be simultaneously formulated or may be contained in the same preparation. Alternatively, metformin or a pharmaceutically acceptable salt thereof, and dihydroquercetin or a pharmaceutically acceptable salt thereof may be separately formulated, and may be administered to a single subject simultaneously or at different time points by the same pathway or different pathways. That is, the medicament of the present invention includes a medicament containing metformin or a pharmaceutically acceptable salt thereof, and dihydroquercetin or a pharmaceutically acceptable salt thereof in a single preparation, and a medicament using a pharmaceutical composition comprising metformin or a pharmaceutically acceptable salt thereof and a pharmaceutical composition comprising dihydroquercetin or a pharmaceutically acceptable salt thereof, which are formulated separately, in combination.

The medicament of the present invention can be formulated into, for example, a pharmaceutical composition such as a tablet (including sugar-coated tablet, film-coated tablet), a powder, a granule, a capsule (including soft capsule), a liquid, an injection, a suppository, a sustained-release preparation (e.g., sustained-release microcapsule), or an immediate-release preparation by, for example, mixing metformin or a pharmaceutically acceptable salt thereof, and/or dihydroquercetin or a pharmaceutically acceptable salt thereof with a pharmacologically acceptable carrier according to a known method, and safely administered orally or parenterally (e.g., topical, rectal, intravenous administration etc.). The injection can be used for intravenous, intramuscular, subcutaneous or intraorgan administration, or can be directly administered to the lesion.

Examples of the pharmacologically acceptable carrier that can be used for the production of the medicament of the present invention include various organic or inorganic carrier substances conventionally used, such as excipient, lubricant, binder and disintegrant for solid preparations, solvent, solubilizing agents, suspending agent, isotonic agent, buffering agent and soothing agent for liquid preparations and the like. Furthermore, where necessary, appropriate amounts of general additives such as preservative, antioxidant, colorant, sweetening agent, adsorbent, wetting agent and the like can also be used.

Examples of the excipient include lactose, sucrose, D-mannitol, starch, cornstarch, crystalline cellulose, light anhydrous silicic acid and the like.

Examples of the lubricant include magnesium stearate, calcium stearate, talc, colloidal silica and the like.

Examples of the binder include crystalline cellulose, sucrose, D-mannitol, dextrin, hydroxypropylcellulose, hydroxypropylmethylcellulose, polyvinylpyrrolidone, starch, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyltriethanolamine, sodium lauryl sulfate, lauryl aminopropionic acid, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerol, D-mannitol and the like.

Examples of the buffering agent include buffers such as phosphate, acetate, carbonate, citrate and the like; and the like.

Examples of the soothing agent include benzyl alcohol and the like.

Examples of the preservative include paraoxybenzoates, chlorobutanol, benzyl alcohol, phenethyl alcohol, dehydroacetic acid, sorbic acid and the like.

Examples of the antioxidant include sulfite, ascorbic acid, α-tocopherol and the like.

The contents of metformin or a pharmaceutically acceptable salt thereof, and dihydroquercetin or a pharmaceutically acceptable salt thereof in the medicament of the present invention can be appropriately selected according to the form of the preparation and the like.

For example, the content of metformin in the medicament of the present invention containing metformin and dihydroquercetin in a single preparation is generally about 0.01 to about 99.99 wt %, preferably about 0.1 to about 50 wt %, relative to the whole preparation, and the content of dihydroquercetin is generally about 0.01 to about 99.99 wt %, preferably about 0.1 to about 50 wt %, relative to the whole preparation.

The content ratio of metformin and dihydroquercetin in the medicament of the present invention is about 0.0005-300 parts by weight, preferably about 0.5-300 parts by weight, more preferably about 0.5-100 parts by weight, still more preferably about 2.5-50 parts by weight, particularly preferably about 2.5-10 parts by weight, of metformin per 1 part by weight of dihydroquercetin.

In addition, the content ratio of metformin and dihydroquercetin in the medicament of the present invention is about 1-600 mol, preferably about 1-200 mol, more preferably about 5-100 mol, still more preferably about 5-20 mol, of metformin per 1 mol of dihydroquercetin.

While the content of the additive such as carrier and the like in the medicament of the present invention varies depending on the form of the preparation, it is generally about 1 to about 99.99 wt %, preferably about 10 to about 90 wt %, relative to the whole preparation.

When metformin and dihydroquercetin are separately formulated, the content of metformin in the preparation containing metformin is generally about 0.01 to about 100 wt %, preferably about 0.1 to about 90 wt %, relative to the whole preparation, and the content of dihydroquercetin in the preparation containing dihydroquercetin is generally about 0.01 to about 100 wt %, preferably about 0.1 to about 90 wt %, relative to the whole preparation. The content of an additive such as carrier and the like is as mentioned above.

The use rate of metformin and dihydroquercetin when they are separately formulated is generally about 0.0005-300 parts by weight, preferably about 0.5-300 parts by weight, more preferably about 0.5-200 parts by weight, still more preferably about 2.5-50 parts by weight, particularly preferably about 2.5-10 parts by weight, of metformin per 1 part by weight of dihydroquercetin.

In addition, the use rate of metformin and dihydroquercetin when they are separately formulated is about 0.001-600 mol, preferably about 1-600 mol, more preferably about 1-200 mol, still more preferably about 1-100 mol, particularly preferably about 5-20 mol, of metformin per 1 mol of dihydroquercetin.

When a pharmaceutically acceptable salt of metformin and/or a pharmaceutically acceptable salt of dihydroquercetin are/is used, the contents thereof in the preparation and the content ratio thereof are within the same range as that indicated above for metformin and dihydroquercetin.

These preparations can be produced by a known method generally used in the preparation steps.

In the case of injection, for example, injections (e.g., Captisol preparation) can be produced by producing an aqueous injection of metformin or a pharmaceutically acceptable salt thereof, and/or dihydroquercetin or a pharmaceutically acceptable salt thereof together with dispersing agents (e.g., Tween 80 (manufactured by Atlas Powder, USA), HCO 60 (manufactured by Nikko Chemicals), polyethylene glycol, carboxymethylcellulose, sodium alginate, hydroxypropylmethylcellulose, dextrin etc.), stabilizers (e.g., ascorbic acid, sodium pyrrosuifite etc.), surfactants (e.g., polysorbate 80, macrogol etc.), solubilizers (e.g., glycerol, ethanol, Captisol (trade name, sulfobutylether-β-cyclodextrin sodium salt) etc.), buffering agents (e.g., citric acid, phosphoric acid and alkali metal salt thereof, citric acid and alkali metal salt thereof etc.), isotonic agents (e.g., sodium chloride, potassium chloride, mannitol, sorbitol, glucose etc.), pH adjusters (e.g., hydrochloric acid, sodium hydroxide etc.), preservatives (e.g., ethyl parahydroxybenzoate, benzoic acid, methyl p-hydroxybenzoate, propyl p-hydroxybenzoate, benzyl alcohol etc.), dissolving agents (e.g., concentrated glycerol, meglumine etc.), solubilizing agents (e.g., propylene glycol, sucrose etc.), soothing agents (e.g., glucose, benzyl alcohol etc.) and the like, or an oily injection by dissolving, suspending or emulsifying them in vegetable oil such as olive oil, sesame oil, cottonseed oil, corn oil and the like, or a solubilizing agent such as propylene glycol and the like.

In the case of oral preparation (tablet), for example, an oral preparation can be produced by mixing metformin or a pharmaceutically acceptable salt thereof, and/or dihydroquercetin or a pharmaceutically acceptable salt thereof and excipients (e.g., lactose, sucrose, starch, cornstarch etc.), disintegrants (e.g., starch, calcium carbonate etc.), binders (e.g., starch, gum arabic, carboxymethylcellulose, polyvinylpyrrolidone, hydroxypropylcellulose, gelatin etc.), lubricants (e.g., talc, magnesium stearate, polyethylene glycol 6000 etc.) and the like, compression molding the mixture, then, where necessary, coating same by a known method for masking of taste, enteric coating or sustainability.

Examples of the coating agent used here include hydroxypropylmethylcellulose, ethylcellulose, hydroxymethylcellulose, hydroxypropylcellulose, polyoxyethyleneglycol, Tween 80, pluronic F68, cellulose acetate phthalate, hydroxypropylmethylcellulose phthalate, hydroxymethylcellulose acetate succinate, Eudragit (manufactured by Rohm, Germany, methacrylic acid-acrylic acid copolymer) and dye (e.g., ferric oxide red, titanium dioxide etc.) and the like. Examples of the sugar coating include sucrose, talc, gum arabic, dye (e.g., ferric oxide red, titanium dioxide etc.), polishing agent (e.g., beeswax etc. and the like.

In the case of suppository, for example, metformin or a pharmaceutically acceptable salt thereof, and/or dihydroquercetin or a pharmaceutically acceptable salt thereof can be formulated into an oily or aqueous solid, semisolid or liquid suppository by using substrates such as oily bases (e.g., glycerides of higher fatty acid [e.g., cacao butter, witepsols (manufactured by Dynamitnovel Ltd., Germany) etc.], medium-chain fatty acids [e.g., miglyols (manufactured by Dynamitnovel Ltd., Germany) etc.], vegetable oils (e.g., sesame oil, soybean oil, cottonseed oil etc.) etc.), aqueous bases (e.g., polyethylene glycols, propylene glycol etc.), aqueous gel bases (e.g., natural gums, cellulose derivative, vinyl polymer, acrylic acid polymer etc.) and the like according to a known method.

The medicament of the present invention shows reduced side effects and can be safely administered to human and animals (e.g., mouse, rat, rabbit, dog, cat, *bovine*, horse, *swine*, monkey etc.).

The dose of the medicament of the present invention can be appropriately selected according to the use, age and sex of the patient, level of the disease and the like. The dose of the medicament of the present invention for an adult (body weight 60 kg) per day is generally about 250-3000 mg, preferably 500-2250 mg, of metformin or a pharmaceutically acceptable salt thereof, and generally about 40-1200 preferably 50-900 mg, of dihydroquercetin or a pharmaceutically acceptable salt thereof. The dose is administered in one to several portions per day.

The medicament of the present invention is useful as a prophylactic or therapeutic agent for a malignant tumor.

Examples of the malignant tumor include childhood brain tumor selected from the group consisting of astroglioma, malignant medulloblastoma, germ cell tumor, craniopharyngioma and ependymoma; adult brain tumor selected from the group consisting of glioma, glial tumor, meningioma, pituitary adenoma and neurinoma; head and neck cancer selected from the group consisting of maxillary sinus cancer, pharyngeal cancer (e.g., nasopharyngeal cancer, oropharyngeal cancer, hypopharyngeal cancer), laryngeal cancer, mouth cavity cancer, lip cancer, tongue cancer and parotid cancer; thoracic cancer and tumor selected from the group consisting of small cell lung cancer, non-small cell lung cancer, lung adenomatosis and mesothelioma; gastrointestinal cancer and tumor selected from the group consisting of esophagus cancer, liver cancer, primary liver cancer, gall bladder cancer, bile duct cancer, gastric cancer, colorectal cancer, colon cancer, rectal cancer, anal cancer, pancreatic cancer and pancreatic endocrine tumor; urinary organ cancer and tumor selected from the group consisting of penile cancer, renal pelvis•ureteral cancer, renal cell cancer, testis tumor (also called orchis tumor), prostate cancer, urinary bladder cancer, Wilms tumor and urothelial cancer; gynecological cancer and tumor selected from the group consisting of vulvar cancer, cervical cancer, uterine body cancer, endometrial cancer, uterus sarcoma, chorionic cancer, vagina cancer, breast cancer, ovarian cancer and ovarian germ cell tumor; adult and childhood soft tissue sarcoma; bone tumor selected from the group consisting of osteosarcoma and Ewing's tumor; cancer and tumor of endocrine tissue selected from the group consisting of adrenal cortex cancer and thyroid cancer; malignant lymphoma and leukemia selected from the group consisting of malignant lymphoma, non-Hodgkin's lymphoma, Hodgkin's disease, multiple myeloma, plasma cell tumor, acute myeloid leukemia, acute lymphatic leukemia, adult T-cell leukemia lymphoma, chronic myeloid leukemia and chronic lymphatic leukemia; and skin cancer and tumor selected from the group consisting of chronic myeloproliferative disease, malignant melanoma, squamous cell cancer, basal cell cancer and mycosis fungoides.

Since the medicament of the present invention has a particularly remarkable anti-malignant tumor effect, it is expected to show an anti-malignant tumor effect for a patient for whom an anti-malignant tumor drug other than metformin and a pharmaceutically acceptable salt thereof, and dihydroquercetin and a pharmaceutically acceptable salt thereof provides only an insufficient effect.

The medicament of the present invention may be further combined with one or more kinds of anti-malignant tumor drugs other than metformin and a pharmaceutically acceptable salt thereof, and dihydroquercetin and a pharmaceutically acceptable salt thereof.

Examples of the anti-malignant tumor drug other than metformin and a pharmaceutically acceptable salt thereof, and dihydroquercetin and a pharmaceutically acceptable salt thereof include a molecule target drug, an alkylating agent, a metabolic antagonist, a plant alkaloid, an anticancer antibiotic, a hormone agent, an immunotherapeutic agent and the like.

Examples of the aforementioned "molecule target drug" include imatinib, gefitinib, erlotinib, sunitinib, sorafenib, brivanib, tivantinib, linifanib, bortezomib, nilotinib, dasatinib, lestaurtinib, lapatinib, thalidomide, lenalidomide, sirolimus, everolimus, temsirolimus, vorinostat, tretinoin, tamibarotene, rituximab, bevacizumab, ramucirumab, panitumumab, cetuximab, trastuzumab, alemtuzumab, gemtuzumab, ozogamicin, ibritumomab tiuxetan, azacitidine, decitabine, zoledronic acid, arsenic trioxide, oblimersen and the like.

Examples of the aforementioned "alkylating agent" include mechlorethamine; cyclophosphamide; ifosfamide; carmustine; busulfan; temozolomide; procarbazine; lomustine; dacarbazine; bendamustine; melphalan; nimustine; ranimustine; chlorambucil; fotemustine; platinum preparations such as oxaliplatin, cisplatin, carboplatin and the like; and the like.

Examples of the aforementioned "metabolic antagonist" include gemcitabine, methotrexate, capecitabine, cytarabine, fludarabine, cladribine, enocitabine, carmofur, tegafur, tegafur.uracil, tegafur-gimeracil.oteracil potassium, 5-fluorouracil, doxifluridine, nelarabine, hydroxycarbamide, pentostatin, mercaptopurine, leucovorin, pemetrexed and the like.

Examples of the aforementioned "plant alkaloid" include topoisomerase inhibitors such as irinotecan, topotecan, nogitecan, etoposide, sobuzoxane and the like; mitotic inhibitors such as paclitaxel, Abraxane (trade name), docetaxel, ixabepilone, vinblastine, vindesine, vincristine, vinorelbine, eribulin and the like; and the like.

Examples of the aforementioned "anticancer antibiotic" include doxorubicin, mitomycin C, mitoxantrone, epirubicin, idarubicin, daunorubicin, aclarubicin, amrubicin, pirarubicin, actinomycin D, bleomycin, peplomycin, cyclosporin and the like.

Examples of the aforementioned "hormone agent" include tamoxifen, anastrozole, letrozole, exemestane, fulvestrant, flutamide, bicalutamide, estramustine, chlormadinone, toremifene, goserelin, prednisone, leuprorelin, abiraterone, dexamethasone and the like.

Examples of the aforementioned "immunotherapeutic agent" include GM-CSF, interferon alpha 2b, interleukin 2, filgrastim, epoetin alfa and the like.

The present invention also relates to a commercial package comprising the above-mentioned "medicament in which metformin or a pharmaceutically acceptable salt thereof, and dihydroquercetin or a pharmaceutically acceptable salt thereof are combined" of the present invention, and a written matter associated therewith, the written matter stating that the medicament can or should be used for the prophylaxis or treatment of a malignant tumor.

The present invention further relates to an agent for reducing the side effect (particularly lactic acidosis) of metformin or a pharmaceutically acceptable salt thereof, which comprises dihydroquercetin or a pharmaceutically acceptable salt thereof as an active ingredient, and an enhancer of an anti-malignant tumor action of metformin or a pharmaceutically acceptable salt thereof, which comprises dihydroquercetin or a pharmaceutically acceptable salt thereof as an active ingredient. The present invention also relates to an agent for reducing the side effect (particularly lactic acidosis) of metformin or a pharmaceutically acceptable salt thereof comprising dihydroquercetin or a pharmaceutically acceptable salt thereof as an active ingredient, which is used in combination with metformin or a pharmaceutically acceptable salt thereof, and an enhancer of an anti-malignant tumor action comprising dihydroquercetin or a pharmaceutically acceptable salt thereof as an active ingredient, which is used in combination with metformin or a pharmaceutically acceptable salt thereof.

In the side effects reducing agent and the anti-malignant tumor action enhancer, examples of "metformin", "metformin or a pharmaceutically acceptable salt thereof", "dihydroquercetin or a pharmaceutically acceptable salt thereof", administration form, dose, subject of administration, target disease and the like are similar to those described for the above-mentioned medicament of the present invention.

(II) Medicament Containing Dihydroquercetin or a Pharmaceutically Acceptable Salt Thereof as an Active Ingredient The present invention relates to a medicament for the prophylaxis or treatment of pancreatic cancer, which contains dihydroquercetin or a pharmaceutically acceptable salt thereof as an active ingredient, and a pancreatic cancer stem cell inhibitor comprising dihydroquercetin or a pharmaceutically acceptable salt thereof as an active ingredient.

Examples of the "dihydroquercetin or a pharmaceutically acceptable salt thereof", administration form, subject of administration and the like are similar to those described for the above-mentioned (I).

The medicament and the inhibitor of the present invention can be formulated into, for example, a pharmaceutical composition such as a tablet (including sugar-coated tablet, filmcoated tablet), a powder, a granule, a capsule (including soft capsule), a liquid, an injection, a suppository, a sustained-release preparation (e.g., sustained-release microcapsule), or an immediate-release preparation by, for example, mixing dihydroquercetin or a pharmaceutically acceptable salt thereof with a pharmacologically acceptable carrier according to a known method, and safely administered orally or parenterally (e.g., topical, rectal, intravenous administration etc.). The injection can be used for intravenous, intramuscular, subcutaneous or intraorgan administration, or can be directly administered to the lesion. The pharmacologically acceptable carrier is similar to those described for the above-mentioned (I).

These preparations can be produced by a known method generally used for the preparation steps.

The content of dihydroquercetin or a pharmaceutically acceptable salt thereof in the medicament and the inhibitor of the present invention can be appropriately selected according to the form of preparation and the like.

For example, the content of dihydroquercetin or a pharmaceutically acceptable salt thereof is generally about 0.01 to about 99.99 wt %, preferably about 0.1 to about 90 wt %, relative to the whole preparation.

While the content of the additive such as carrier and the like in the medicament and the inhibitor of the present invention varies depending on the form of the preparation, it is generally about 1 to about 99.99 wt %, preferably about 10 to about 90 wt %, relative to the whole preparation.

The medicament and the inhibitor of the present invention preferably contain metformin or a pharmaceutically acceptable salt thereof, since metformin or a pharmaceutically acceptable salt thereof produces a synergistic anti-malignant tumor effect. The "metformin or a pharmaceutically acceptable salt thereof" is similar to those described for the above-mentioned (I).

The content of metformin or a pharmaceutically acceptable salt thereof is generally about 0.5 to about 100 wt %, preferably about 2.5 to about 50 wt %, more preferably about 2.5 to about 10 wt %, per 1 part by weight of dihydroquercetin.

The medicament and the inhibitor of the present invention can be used in combination with gemcitabine.

The dose of gemcitabine can be determined according to the dose of commercially available gemcitabine preparations.

The dose of the medicament and the inhibitor of the present invention can be appropriately selected according to the use, age and sex of the patient, level of the disease and the like. The dose for an adult (body weight 60 kg) per day is generally about 40-1200 mg, preferably about 50-900 mg, more preferably about 100-1050 mg, of dihydroquercetin or a pharmaceutically acceptable salt thereof. The dose is administered in one to several portions per day.

EXAMPLES

The present invention is explained in detail in the following by referring to Examples, which are not to be construed as limitative.

[Example 1] The Suppressive Effect on Proliferation-Related Signal Pathway by Combined Use of Metformin and Dihydroquercetin in a Human Lung Cancer Cell Line NCI-H1299 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet.

2) Preparation of Test Substances

Metformin was dissolved in RPMI-1640 medium containing 10% inactivated (56° C., 30 min treatment) fetal *bovine* serum (hereinafter to be abbreviated as 20% FBS-RPMI1640 medium) (NACALAI TESQUE, INC.) to prepare 200 mmol-/L metformin (final concentration 20 mmol/L). Dihydroquercetin was dissolved in ethanol, and diluted with medium to prepare 5 mmol/L dihydroquercetin (final concentration 0.5 mmol/L).

3) Cell

The human lung cancer-derived cell line NCI-H1299 was obtained from. American Type Culture Collection (ATCC) (catalog no. CRL-5803, Cancer Res, 1992; 52 (9 Suppl): 2732s-2736s). The cells were cultured in 10% FES-RPMI1640 medium under the conditions of 37° C., 5% $CO_2$.

4) Addition of Test Substances and Measurement

On the following day after cell seeding, test substances were added and the cells were cultured for 6 hr before harvesting them. The amounts of relative phospho-4E-BP1 protein contained in the prepared whole cell lysates were measured and evaluated. Each group (N=3) was treated as follows:

(1) Control (vehicle control) group: 1% ethanol containing medium
(2) Metformin single-treated group: metformin 20 mmol/L
(3) Dihydroquercetin single-treated group: dihydroquercetin 0.5 mmol/L
(4) Combined-treated group: metformin 20 mmol/L+dihydroquercetin 0.5 mmol/L The passage-cultured NCI-H1299 cells were dissociated with trypsin, and suspended in fresh medium. The cell density of the cell suspension was determined using a hematocytometer and adjusted to $1\times10^6$ cells/mL. The cells were seeded on 12-well multiwell culture plate (IWAKI) at 0.5 mL per well, and cultured overnight under the conditions of 37° C., 5% $CO_2$. On the following day, medium containing metformin or dihydroquercetin or both metformin and dihydroquercetin, at the given concentration, was added into each well. After incubation for 6 hr, the cells in each well were washed twice with Dulbecco's phosphate buffered saline (D-PBS), and whole cell lysates were prepared using cell lysis buffer (Cell Signaling Technology, Inc.). Upon centrifugation, the supernatants were sampled, and the amounts of relative phospho-4E-BP1 (Thr37/Thr46) protein in the samples were quantified using ELISA kits (Cell Signaling Technology, Inc., catalog No. 7854). The concentrations of the total protein in the cell extract were measured using BCA protein assay (Pierce), and the relative phospho-4E-BP1 protein amount of each well was normalized with the total protein amount.

5) Statistical Analysis

The results are shown in mean value (MEAN)±standard deviation (SD).

To evaluate the influence of the combined use on relative phospho-4E-BP1 protein amount, the Dunnett test was performed to compare the combined-treated group with each single agent-treated group. When a significant difference was observed in the combined-treated group against each single agent treated group, two-way ANOVA (two-tailed) (factors: group and concentration) was performed to evaluate the synergistic effect between the metformin-treated groups (groups 1 and 2) and the dihydroquercetin-treated groups (groups 3 and 4). The analysis was performed using SAS Software Release 9.3 (SAS Institute Japan). The differences were considered statistically significant when the p value was less than 0.05.

6) Results

The combined use of metformin and dihydroquercetin suppressed the relative phospho-4E-BP1 protein amount significantly stronger than each single compound group (FIG. 1)

7) Conclusion

In NCI-H1299 cells, a synergistic suppressive effect on proliferation-related signal pathway by the combined use of metformin and dihydroquercetin was observed. This indicated the usefulness of a combination of metformin and dihydroquercetin in cancer chemotherapy.

[Example 2] The Suppressive Effect on Cancer Cell Proliferation-Related Signal Pathway by Combined Use of Metformin and Dihydroquercetin in a Human Pancreatic Cancer Cell Line AsPC-1 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet.

2) Preparation of Test Substances

Metformin was dissolved in 10% FBS-RPMI1640 medium to prepare 200 mmol/L metformin (final concentration 20 mmol/L). Dihydroquercetin was dissolved in ethanol, and diluted with medium to prepare 2 mmol/L dihydroquercetin (final concentration 0.2 mmol/L).

3) Cell

Human pancreatic cancer-derived cell line AsPC-1 was obtained from Dainippon Pharmaceutical Co., Ltd. (now DS PHARMA BIOMEDICAL CO., LTD., In Vitro. 1982; 18: 24-34). The cells were cultured in a 10% FBS-RPMI1640 medium under the conditions of 37° C., 5% $CO_2$.

4) Addition of Test Substances and Measurement

On the following day after cell seeding, test substances were added and the cells were cultured for 6 hr before harvesting them. The amounts of relative phospho-4E-BP1 protein contained in the prepared whole cell lysates were measured and evaluated. Each group (N=3) was treated as follows:

(1) Control (vehicle control) group: 1% ethanol containing medium
(2) Metformin single-treated group: metformin 20 mmol/L
(3) Dihydroquercetin single-treated group: dihydroquercetin 0.2 mmol/L
(4) Combined-treated group: metformin 20 mmol/L+dihydroquercetin 0.2 mmol/L The passage-cultured AsPc-1 cells were dissociated with trypsin, and suspended in fresh medium. The cell density of the cell suspension was determined using a hematocytometer and adjusted to $1\times10^6$ cells/mL. The cells were seeded on 12-well multiwell culture plate at 0.5 mL per well, and cultured overnight under the conditions of 37° C., 5% $CO_2$. On the following day, medium containing metformin or dihydroquercetin or both metformin and dihydroquercetin, at the given concentration, was added into each well. After incubation for 6 hr, the cells in each well were washed twice with D-PBS, and whole cell lysates were prepared using cell lysis buffer. Upon centrifugation, the supernatants were sampled, and the amounts of relative phospho-4E-BP1 (Thr37/Thr46) protein in the samples were quantified using ELISA kits in the same manner as in Example 1. The concentrations of the total protein in the whole cell lysates were measured using BCA protein assay, and the relative phospho-4E-BP1 protein amount of each well was normalized with the total protein amount.

5) Statistical Analysis

The results are shown in mean value (MEAN)±standard deviation (SD).

To evaluate the influence of the combined use on relative phospho-4E-BP1 protein amount, the Dunnett test was performed to compare the combined-treated group with each single agent-treated group. When a significant difference was observed in the combined-treated group against each single agent-treated group, two-way ANOVA (two-tailed) (factors: group and concentration) was performed to evaluate the synergistic effect between the metformin-treated groups (groups 1 and 2) and the dihydroquercetin-treated groups (groups 3 and 4). The analysis was performed using SAS Software Release 9.3 (SAS Institute Japan). The differences were considered statistically significant when the p value was less than 0.05.

6) Results

Figure 2:
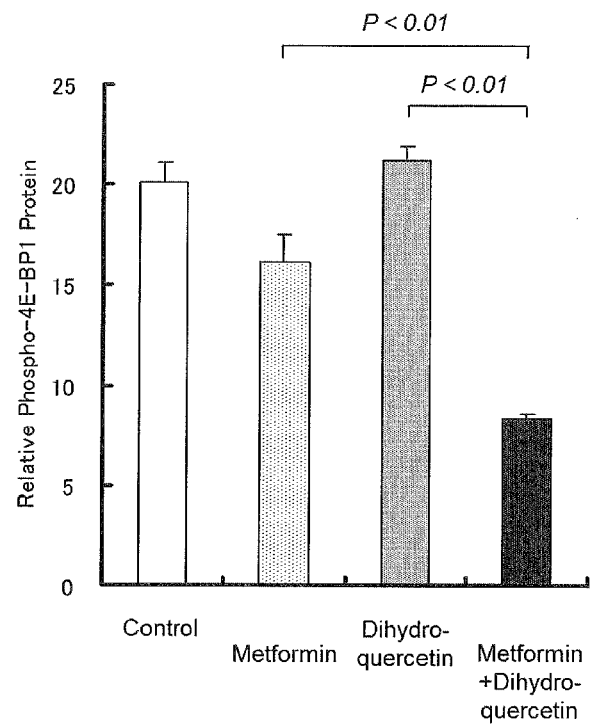
FIG. 2 shows the results of Example 2.

The combined use of metformin and dihydroquercetin suppressed the relative phospho-4E-BP1 protein amount significantly stronger than each single compound group (FIG. 2).

7) Conclusion

In AsPC-1 cells, a synergistic suppressive effect on proliferation-related signal pathway by the combined use of metformin and dihydroquercetin was observed. This indicated the usefulness of a combination of metformin and dihydroquercetin in cancer chemotherapy.

[Example 3] The Suppressive Effect of Dihydroquercetin on Metformin-Induced Lactate Production in a Human Lung Fibroblast Cell Line WI-38 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet.

2) Preparation of Test Substances

Metformin was dissolved in 10% FBS-RPMI1640 medium to prepare 200 mmol/L metformin (final concentration 20 mmol/L). Dihydroquercetin was dissolved in ethanol, and diluted with medium to prepare 10 mmol/L dihydroquercetin (final concentration 1 mmol/L).

3) Cell

Human lung fibroblast-derived cell line WI-38 was obtained from ATCC (catalog no. CCL-75, Exp. Cell, Res., 25: 585-621, 1961). The cells were cultured in 10% FBS-RPMI1640 medium under the conditions of 37° C., 5% $CO_2$.

4) Addition of Test Substances and Measurement

On the following day after cell seeding, dihydroquercetin was added and the cells were cultured for 1 hr. Then, metformin was added and the cells were cultured for 6 hr. After the culture, the conditioned medium was sampled, and the concentration of lactate contained in the medium was measured and evaluated. Each group (N=3) was treated as follows:

(1) Control (vehicle control) group: 1% ethanol containing medium
(2) Metformin single-treated group: metformin 20 mmol/L
(3) Dihydroquercetin and Metformin combined-treated group: metformin 20 mmol/L+dihydroquercetin 1 mmol/L The passage-cultured WI-38 cells were dissociated with trypsin, and suspended in fresh medium. The cell density of the cell suspension was determined using a hematocytometer and adjusted to $2.5 \times 10^5$ cells/mL. The cells were seeded on 24-well multiwell culture plate (IWAKI) at 0.5 mL per well, and cultured overnight under the conditions of 37° C., 5% $CO_2$. Medium containing the given concentration of dihydroquercetin was added to each well and the cells were cultured for 1 hr. Then, medium containing the given concentration of metformin was added and the cells were further cultured for 6 hr. After the culture, the culture supernatant from each well was sampled and passed through a filter for molecular weight cut-off 10 kDa to obtain the filtrate. Using the Lactate Assay Kit II (BioVision) catalog no. K627-100, lactate concentration was measured. The cells after sampling of the culture supernatant were washed twice with D-PBS, and cell lysis buffer was added to prepare whole cell lysates. The concentrations of the protein in the whole cell lysates were measured by BCA protein assay, and the lactate concentration of each well was normalized with the protein concentration.

5) Statistical Analysis

The results are shown in mean value (MEAN)±standard deviation (SD).

To evaluate the influence of dihydroquercetin on metformin-induced produced lactate content, a Student's t-test was performed for the concentration of lactate in the medium between the metformin single treated group and the combined-treated group. When the value in the combined-treated group is significantly lower compared with the metformin single treated group, dihydroquercetin is defined as having a suppressive effect on the content. The analysis was performed using SAS software Release 9.3 (SAS Institute Japan). The differences were considered statistically significant when the p value was less than 0.05.

6) Results

Figure 3:
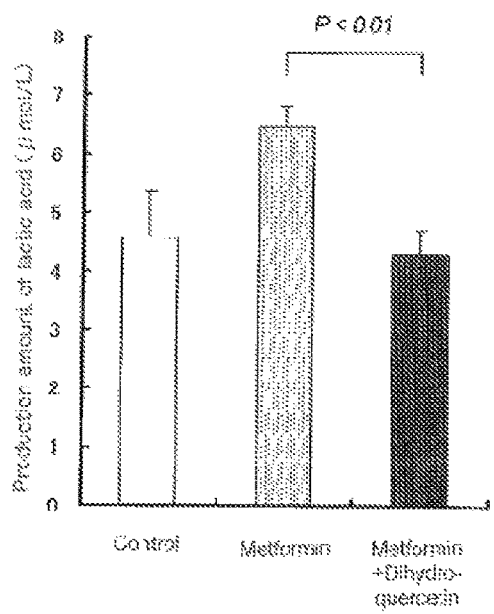
FIG. 3 shows the results of Example 3.

Metformin induced production of lactate in WI-38 cells. Dihydroquercetin significantly suppressed the lactate production induced by metformin (FIG. 3).

7) Conclusion

In WI-38 cells, a suppressive effect of dihydroquercetin on metformin-induced lactate production was observed. This indicated a clinical usefulness of dihydroquercetin in reducing the risk of lactic acidosis caused by metformin.

[Example 4] The Suppressive Effect on Cancer Cell Proliferation-Related Signal Pathway by Combined Use of Metformin and Dihydroquercetin in a Human Liver Cancer Cell Line HuH-7 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet.

2) Preparation of Test Substances

Metformin was dissolved in 10% FBS-RPMI1640 medium to prepare 50 mmol/L metformin (final concentration 5 mmol/L). Dihydroquercetin was dissolved in ethanol, and diluted with medium to prepare 2 mmol/L dihydroquercetin (final concentration 0.2 mmol/L).

3) Cell

Human liver cancer-derived cell line HuH-7 was obtained from Health Science Research Resources Bank (Cancer Res. 1982; 42 (9): 3858-63). The cells were cultured in 10% FBS-RPMI1640 medium under the conditions of 37° C., 5% $CO_2$.

4) Addition of Test Substances and Measurement

On the following day after cell seeding, test substances were added and the cells were cultured for 6 hr before harvesting them. The amounts of relative phospho-4E-BP1 protein contained in the prepared whole cell lysates were measured and evaluated. Each group (N=3) was treated as follows:

(1) Control (vehicle control) group: 1% ethanol containing medium
(2) Metformin single-treated group: metformin 5 mmol/L
(3) Dihydroquercetin single-treated group: dihydroquercetin 0.2 mmol/L
(4) Combined-treated group: metformin 5 mmol/L+dihydroquercetin 0.2 mmol/L The passage-cultured HuH-7 cells were dissociated with trypsin, and suspended in fresh medium. The cell density of the cell suspension was determined using a hematocytometer and adjusted to $2.5 \times 10^5$ cells/mL. The cells were seeded on 12-well multiwell culture plate at 1 mL per well, and cultured overnight under the conditions of 37° C., 5% $CO_2$. On the following day, medium containing metformin or dihydroquercetin or both metformin and dihydroquercetin, at the given concentration, was added into each well. After incubation for 6 hr, the cells in each well were washed twice with D-PBS, and whole cell lysates were prepared using cell lysis buffer. Upon centrifugation, the supernatants were sampled, and the amounts of relative phospho-4E-BP1 (Thr37/Thr46) protein in the samples were quantified using ELISA kits in the same manner as in Example 1. The concentrations of the total protein in the whole cell lysates were measured using BCA protein assay, and the relative phospho-4E-BP1 protein amount of each well was normalized with the total protein amount.

5) Statistical Analysis

The results are shown in mean value (MEAN)±standard deviation (SD).

To evaluate the influence of the combined use on the relative phospho-4E-BP1 protein amount, the Dunnett test was performed to compare the combined-treated group with each single agent treated group. When a significant difference was observed in the combined-treated group against each single agent-treated group, two-way ANOVA (two-tailed) (factors: group and concentration) was performed to evaluate the synergistic effect between the metformin-treated groups (groups 1 and 2) and the dihydroquercetin-treated groups (groups 3 and 4). The analysis was performed using SAS Software Release 9.3 (SAS Institute Japan). The differences were considered statistically significant when the p value was less than 0.05.

6) Results

The results are shown in Table 1.

The combined use of metformin and dihydroquercetin suppressed the relative phospho-4E-BP1 protein amount significantly stronger than each single compound group.

TABLE 1

| | Relative phospho-4E-BP1 protein amount | |
|---|---|---|
| | MEAN | SD |
| Control | 84.1 | 2.1 |
| Metformin | 61.7 | 3.5 |
| Dihydroquercetin | 59.7 | 1.6 |
| Metformin + Dihydroquercetin | 28.2 | 2.6 |

7) Conclusion

In HuH-7 cells, a synergistic suppressive effect of cancer cell proliferation-related signal pathway by the combined use of metformin and dihydroquercetin was observed. This indicated the usefulness of a combination of metformin and dihydroquercetin in cancer chemotherapy.

[Example 5] The Suppressive Effect on Cancer Cell Proliferation-Related Signal Pathway by Combined Use of Metformin and Dihydroquercetin in a Human Breast Cancer Cell Line MDA-MB-231 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet.

2) Preparation of Test Substances

Metformin was dissolved in 10% FBS-RPMI1640 medium to prepare 50 mmol/L metformin (final concentration 5 mmol/L). Dihydroquercetin was dissolved in ethanol, and diluted with medium to prepare 2 mmol/L, dihydroquercetin (final concentration 0.2 mmol/L).

3) Cell

Human breast cancer-derived cell line MDA-MB-231 was obtained from ATOC (J Natl Cancer Inst. 1974; 53 (3): 661-74). The cells were cultured in 10% FBS-RPMI1640 medium under the conditions of 37° C., 5% $CO_2$.

4) Addition of Test Substances and Measurement

On the following day after cell seeding, test substances were added and the cells were cultured for 6 hr before harvesting them. The amounts of relative phospho-4E-BP1 protein contained in the prepared whole cell lysates were measured and evaluated. Each group (N=3) was treated as follows:

(1) Control (vehicle control) group: 1% ethanol containing medium
(2) Metformin single-treated group: metformin 5 mmol/L
(3) Dihydroquercetin single-treated group: dihydroquercetin 0.2 mmol/L
(4) Combined-treated group: metformin 5 mmol/L+dihydroquercetin 0.2 mmol/L The passage-cultured MDA-MB-231 cells were dissociated with trypsin, and suspended in fresh medium. The cell density of the cell suspension was determined using a hematocytomotor and adjusted to $2.5 \times 10^5$ cells/mL. The cells were seeded on 12-well multiwell culture plate at 1 mL per well, and cultured overnight under the conditions of 37° C., 5% $CO_2$. On the following day, medium containing metformin or dihydroquercetin or both metformin and dihydroquercetin, at the given concentration, was added into each well. After incubation for 6 hr, the cells in each well were washed twice with D-PBS, and whole cell lysates were prepared using cell lysis buffer. Upon centrifugation, the supernatants were sampled, and the amounts of relative phospho-4E-BP1 (Thr37/Thr46) protein in the samples were quantified using ELISA kits in the same manner as in Example 1. The concentrations of total protein in the whole cell lysates were measured using BOA protein assay, and the relative phospho-4E-BP1 protein amount of each well was normalized with the total protein amount.

5) Statistical Analysis

The results are shown in mean value (MEAN)±standard deviation (SD).

To evaluate the influence of the combined use on the relative phospho-4E-BP1 protein amount, the Dunnett test was performed to compare the combined-treated group with each single agent treated group. When a significant difference was observed in the combined-treated group against each single agent-treated group, two-way ANOVA (two-tailed) (factors: group and concentration) was performed to evaluate the synergistic effect between the metformin-treated groups (groups 1 and 2) and the dihydroquercetin-treated groups (groups 3 and 4). The analysis was performed using SAS Software Release 9.3 (SAS Institute Japan). The differences were considered statistically significant when the p value was less than 0.05.

6) Results

The results are shown in Table 2.

The combined use of metformin and dihydroquercetin suppressed the relative phospho-4E-BP1 protein amount significantly stronger than each single compound group.

TABLE 2

| | Relative phospho-4E-BP1 protein amount | |
|---|---|---|
| | MEAN | SD |
| Control | 33.3 | 3.1 |
| Metformin | 37.1 | 3.1 |
| Dihydroquercetin | 25.9 | 0.6 |
| Metformin + Dihydroquercetin | 19.8 | 1.4 |

7) Conclusion

In MDA-MB-231 cells, a synergistic suppressive effect on proliferation-related signal pathway by the combined use of metformin and dihydroquercetin was observed. This indicated the usefulness of a combination of metformin and dihydroquercetin in cancer chemotherapy.

[Example 6] The Suppressive Effect on Cancer Cell Proliferation-Related Signal Pathway by Combined Use of Metformin and Dihydroquercetin in a Human Prostate Cancer Cell Line 22Rv1 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet.

2) Preparation of Test Substances

Metformin was dissolved in 10% FBS-RPMI1640 medium to prepare 100 mmol/L metformin (final concentration 10 mmol/L). Dihydroquercetin was dissolved in ethanol, and diluted with medium to prepare 2 mmol/L dihydroquercetin (final concentration 0.2 mmol/L).

3) Cell

Human prostate cancer-derived cell line 22Rv1 was obtained from ATCC (In Vitro Cell Dev Biol Anim. 1999; 35 (7): 403-9). The cells were cultured in 10% FBS-RPMI1640 medium under the conditions of 37° C., 5% $CO_2$.

4) Addition of Test Substances and Measurement

On the following day after cell seeding, test substances were added and the cells were cultured for 6 hr before harvesting them. The amounts of relative phospho-4E-BP1 protein contained in the prepared whole cell lysates were measured and evaluated. Each group (N=3) was treated as follows:

(1) Control (vehicle control) group: 1% ethanol containing medium
(2) Metformin single-treated group: metformin 10 mmol/L (3) Dihydroquercetin single-treated group: dihydroquercetin 0.2 mmol/L
(4) Combined-treated group: metformin 10 mmol/L+dihydroquercetin 0.2 mmol/L The passage-cultured 22Rv1 cells were dissociated with trypsin, and suspended in fresh medium. The cell density of the cell suspension was determined using a hematocytometer and adjusted to $2.5 \times 10^5$ cells/mL. The cells were seeded on 12-well multiwell culture plate at 1 mL per well, and cultured overnight under the conditions of 37° C., 5% $CO_2$. On the following day, medium containing metformin or dihydroquercetin or both metformin and dihydroquercetin, at the given concentration, was added into each well. After incubation for 6 hr, the cells in each well were washed twice with D-PBS, and whole cell lysates were prepared using cell lysis buffer. Upon centrifugation, the supernatants were sampled, and the amounts of relative phospho-4E-BP1 (Thr37/Thr46) protein in the samples were quantified using ELISA kits in the same manner as in Example 1. The concentrations of total protein in the whole cell lysates were measured using BCA protein assay, and the relative phospho-4E-BP1 protein amount of each well was normalized with the total protein amount.

5) Statistical Analysis

The results are shown in mean value (MEAN)±standard deviation (SD).

To evaluate the influence of the combined use on the relative phospho-4E-BP1 protein amount, the Dunnett test was performed to compare the combined-treated group with each single agent treated group. When a significant difference was observed in the combined-treated group against each single agent-treated group, two-way ANOVA (two-tailed) (factors: group and concentration) was performed to evaluate the synergistic effect between the metformin-treated groups (groups 1 and 2) and the dihydroquercetin-treated groups (groups 3 and 4). The analysis was performed using SAS Software Release 9.3 (SAS Institute Japan). The differences were considered statistically significant when the p value was less than 0.05.

6) Results

The results are shown in Table 3.

The combined use of metformin and dihydroquercetin suppressed the relative phospho-4E-BP1 protein amount significantly stronger than each single compound group.

TABLE 3

|  | Relative phospho-4E-BP1 protein amount | |
| --- | --- | --- |
|  | MEAN | SD |
| Control | 51.0 | 6.7 |
| Metformin | 57.3 | 2.2 |
| Dihydroquercetin | 53.1 | 4.5 |
| Metformin + Dihydroquercetin | 36.2 | 1.5 |

7) Conclusion

In 22Rv1 cells, a synergistic suppressive effect on proliferation-related signal pathway by the combined use of metformin and dihydroquercetin was observed. This indicated the usefulness of a combination of metformin and dihydroquercetin in cancer chemotherapy.

[Example 7] The Suppressive Effect on Cancer Cell Proliferation-Related Signal Pathway by Combined Use of Metformin and Dihydroquercetin in a Human Bile Duct Cancer Cell Line HuH-28 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet.

2) Preparation of Test Substances

Metformin was dissolved in 10% FBS-RPMI1640 medium to prepare 200 mmol/L metformin (final concentration 20 mmol/L). Dihydroquercetin was dissolved in ethanol, and diluted with medium to prepare 2 mmol/L dihydroquercetin (final concentration 0.2 mmol/L).

3) Cell

Human bile duct cancer-derived cell line HuH-28 was obtained from Health Science Research Resources Bank (Res Exp Med (Berl). 1988; 188 (5): 367-75). The cells were cultured in 10% FBS-RPMI1640 medium under the conditions of 37° C., 5% $CO_2$.

4) Addition of Test Substances and Measurement

On the following day after cell seeding, test substances were added and the cells were cultured for 6 hr before harvesting them. The amounts of relative phospho-4E-BP1 protein contained in the prepared whole cell lysates were measured and evaluated. Each group (N=3) was treated as follows:

(1) Control (vehicle control) group: 1% ethanol containing medium
(2) Metformin single-treated group: metformin 20 mmol/L
(3) dihydroquercetin single-treated group: dihydroquercetin 0.2 mmol/L
(4) combined-treated group: metformin 20 mmol/L+dihydroquercetin 0.2 mmol/L The passage-cultured HuH-28 cells were dissociated with trypsin, and suspended in the medium. The cell density of the cell suspension was determined using a hematocytometer and adjusted to $2.5 \times 10^5$ cells/mL. The cells were seeded on 12-well multiwell culture plate at 1 mL per well, and cultured overnight under the conditions of 37° C., 5% $CO_2$. On the following day, medium containing metformin or dihydroquercetin or both metformin and dihydroquercetin, at the given concentration, was added into each well. After incubation for 6 hr, the cells in each well were washed twice with D-PBS, and whole cell lysates were prepared using a cell lysis buffer. Upon centrifugation, the supernatants were sampled, and the amounts of relative phospho-4E-BP1 (Thr37/Thr46) protein in the samples were quantified using ELISA kits in the same manner as in Example 1. The total protein concentrations in the whole cell lysates were measured using BCA protein assay, and the relative phospho-4E-BP1 protein amount of each well was normalized with the total protein amount.

5) Statistical Analysis

The results are shown in mean value (MEAN)±standard deviation (SD).

To evaluate the influence of the combined use on the relative phospho-4E-BP1 protein amount, the Dunnett test was performed to compare the combined-treated group with each single agent treated group. When a significant difference was observed in the combined-treated group against each single agent-treated group, two-way ANOVA (two-tailed) (factors: group and concentration) was performed to evaluate the synergistic effect between the metformin-treated groups (groups 1 and 2) and the dihydroquercetin-treated groups (groups 3 and 4). The analysis was performed using SAS Software Release 9.3 (SAS Institute Japan.). The differences were considered statistically significant when the p value was less than 0.05.

6) Results

The results are shown in Table 4.

The combined use of metformin and dihydroquercetin suppressed the relative phospho-4E-BP1 protein amount significantly stronger than each single compound group.

TABLE 4

|  | Relative phospho-4E-BP1 protein amount | |
|---|---|---|
|  | MEAN | SD |
| Control | 58.8 | 2.8 |
| Metformin | 55.2 | 1.5 |
| Dihydroquercetin | 54.2 | 0.2 |
| Metformin + Dihydroquercetin | 36.6 | 1.3 |

7) Conclusion

In RuH-28 cells, a synergistic suppressive effect on proliferation-related signal pathway by the combined use of metformin and dihydroquercetin was observed. This indicated the usefulness of a combination of metformin and dihydroquercetin in cancer chemotherapy.

[Example 8] The Suppressive Effect on Cancer Cell Proliferation-Related Signal Pathway by Combined Use of Metformin and Dihydroquercetin in a Human Ovarian Cancer Cell Line Caov-3 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet.

2) Preparation of Test Substances

Metformin was dissolved in 10% FBS-RPMI1640 medium to prepare 200 mmol/L metformin (final concentration 20 mmol/L). Dihydroquercetin was dissolved in ethanol, and diluted with medium to prepare 2 mmol/L dihydroquercetin (final concentration 0.2 mmol/L).

3) Cell

Human ovarian cancer-derived cell line Caov-3 was obtained from ATCC (GYNECOL ONCOL. 1994; 53(1): 70-7). The cells were cultured in 10% FBS-RPMI1640 medium under the conditions of 37° C., 5% $CO_2$.

4) Addition of Test Substances and Measurement

On the following day after cell seeding, test substances were added and the cells were cultured for 6 hr before harvesting them. The amounts of relative phospho-4E-BP1 protein contained in the prepared whole cell lysates were measured and evaluated. Each group (N=3) was treated as follows:

(1) Control (vehicle control) group: 1% ethanol containing medium
(2) Metformin single-treated group: metformin 20 mmol/L
(3) Dihydroquercetin single-treated group: dihydroquercetin 0.2 mmol/L
(4) Combined-treated group: metformin 20 mmol/L+dihydroquercetin 0.2 mmol/L The passage-cultured Caov-3 cells were dissociated with trypsin, and suspended in fresh medium. The cell density of the cell suspension was determined using a hematocytometer and adjusted to $2.5 \times 10^5$ cells/mL. The cells were seeded on 12-well multiwell culture plate at 1 mL per well, and cultured overnight under the conditions of 37° C., 5% $CO_2$. On the following day, medium containing metformin or dihydroquercetin or both metformin and dihydroquercetin, at the given concentration, was added into each well. After incubation for 6 hr, the cells in each well were washed twice with D-PBS, and whole cell lysates were prepared using cell lysis buffer. Upon centrifugation, the supernatants were sampled, and the amounts of relative phospho-4E-BP1 (Thr37/Thr46) protein in the samples were quantified using ELISA kits in the same manner as in Example 1. The total protein concentrations in the whole cell lysates were measured using BCA protein assay, and the relative phospho-4E-BP1 protein amount of each well was normalized with the total protein amount.

5) Statistical Analysis

The results are shown in mean value (MEAN)±standard deviation (SD).

To evaluate the influence of the combined use on the relative phospho-4E-BP1 protein amount, the Dunnett test was performed to compare the combined-treated group with each single agent treated group. When a significant difference was observed in the combined-treated group against each single agent-treated group, two-way ANOVA (two-tailed) (factors: group and concentration) was performed to evaluate the synergistic effect between the metformin-treated groups (groups 1 and 2) and the dihydroquercetin-treated groups (groups 3 and 4). The analysis was performed using SAS Software Release 9.3 (SAS Institute Japan). The differences were considered statistically significant when the p value was less than 0.05.

6) Results

The results are shown in Table 5.

The combined use of metformin and dihydroquercetin suppressed the relative phospho-4E-BP1 protein amount significantly stronger than each single compound group.

TABLE 5

|  | Relative phospho-4E-BP1 protein amount | |
|---|---|---|
|  | MEAN | SD |
| Control | 21.6 | 2.7 |
| Metformin | 22.0 | 0.3 |
| Dihydroquercetin | 21.0 | 1.0 |
| Metformin + Dihydroquercetin | 16.8 | 0.3 |

7) Conclusion

In Caov-3 cells, a synergistic suppressive effect on proliferation-related signal pathway by the combined use of metformin and dihydroquercetin was observed. This indicated the usefulness of a combination of metformin and dihydroquercetin in cancer chemotherapy.

[Example 9] The Suppressive Effect on Cancer Cell Proliferation-Related Signal Pathway by Combined Use of Metformin and Dihydroquercetin in a Human Pancreatic Cancer Cell Line AsPC-1 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet.

2) Preparation of Test Substances

Metformin was dissolved in 10% FBS-RPMI1640 medium to prepare 15, 30 and 60 mmol/L metformin (final concentrations 1.5, 3 and 6 mmol/L). Dihydroquercetin was dissolved in ethanol, and diluted with medium to prepare 3 mmol/L dihydroquercetin (final concentration 0.3 mmol/L).

3) Cell

Human pancreatic cancer-derived cell line AsPC-1 was obtained from DS PHARMA BIOMEDICAL CO., LTD. The cells were cultured in 10% FBS-RPMI1640 medium under the conditions of 37° C., 5% $CO_2$.

4) Addition of Test Substances and Measurement

Each group (N=3) was treated as follows.

(1) Control (vehicle control) group: 1% ethanol containing medium (2) Metformin single-treated group: metformin 1.5, 3 and 6 mmol/L (3) Dihydroquercetin-single treated group: dihydroquercetin 0.3 mmol/L (4) Combined-treated group: metformin 1.5, 3 and 6 mmol/L+dihydroquercetin 0.3 mmol/L The passage-cultured AsPC-1 cells were dissociated with trypsin, and suspended in fresh medium. The cell density of the cell suspension was determined using a hematocytometer and adjusted to $2.5 \times 10^5$ cells/mL. The cells were seeded on 12-well multiwell culture plate at 1 mL per well, and cultured overnight under the conditions of 37° C., 5% $CO_2$. On the following day, medium containing metformin or dihydroquercetin or both metformin and dihydroquercetin, at the given concentration, was added into each well. After incubation under the conditions of 37° C., 5% $CO_2$ for 24 hr, the cells in each well were washed twice with D-PBS, and whole cell lysates were prepared using cell lysis buffer. Upon centrifugation, the supernatants were sampled, and the amounts of relative phospho-4E-BP1 (Thr37/Thr46) protein in the samples were quantified using ELISA kits in the same manner as in Example 1. The concentrations of total protein in the whole cell lysates were measured using BCA protein assay, and the relative phospho-4E-BP1 protein amount of each well was normalized with the total protein amount.

5) Statistical Analysis

The results are shown in mean value (MEAN)±standard deviation (SD).

To evaluate the influence of the combined use on relative phospho-4E-BP1 protein amount, Dunnett test was performed to compare the combined-treated group with each single agent-treated group. When a significant difference was observed in the combined-treated group against each single agent-treated group, two-way ANOVA (two-tailed) (factors: group and concentration) was performed to evaluate the synergistic effect between the metformin-treated groups (groups 1 and 2) and the dihydroquercetin-treated groups (groups 3 and 4). The analysis was performed using SAS Software Release 9.3 (SAS Institute Japan). The differences were considered statistically significant when the p value was less than 0.05.

6) Results

The results are shown in Tables 6-8.

The combined use of metformin and dihydroquercetin suppressed the relative phospho-4E-BP1 protein amount significantly stronger than each single compound group.

TABLE 6 metformin:dihydroquercetin = 1.5 mmol/L:0.3 mmol/L

| | Relative phospho-4E-BP1 protein amount | |
|---|---|---|
| | MEAN | SD |
| Control | 107.3 | 9.3 |
| Metformin | 83.1 | 5.5 |
| Dihydroquercetin | 97.4 | 9.6 |
| Metformin + Dihydroquercetin | 31.2 | 4.1 |

TABLE 7 metformin:dihydroquercetin = 3 mmol/L:0.3 mmol/L

| | Relative phospho-4E-BP1 protein amount | |
|---|---|---|
| | MEAN | SD |
| Control | 33.5 | 10.1 |
| Metformin | 36.9 | 1.7 |
| Dihydroquercetin | 37.2 | 2.5 |
| Metformin + Dihydroquercetin | 18.4 | 0.9 |

TABLE 8 metformin:dihydroquercetin = 6 mmol/L:0.3 mmol/L

| | Relative phospho-4E-BP1 protein amount | |
|---|---|---|
| | MEAN | SD |
| Control | 107.3 | 9.3 |
| Metformin | 83.1 | 5.5 |
| Dihydroquercetin | 89.7 | 7.1 |
| Metformin + Dihydroquercetin | 29.4 | 1.2 |

7) Conclusion

In AsPC-1 cells, a synergistic suppressive effect on proliferation-related signal pathway by the combined use of metformin and dihydroquercetin was observed. This indicated the usefulness of a combination of metformin and dihydroquercetin in cancer chemotherapy.

[Example 10] The Suppressive Effect of Dihydroquercetin on Metformin-Induced Lactate Production in a Human Lung Fibroblast Cell Line WI-38 (In Vitro)

1) Test Substances

Metformin was purchased from Wako Pure Chemical Industries, Ltd. Racemate of dihydroquercetin ((2R,3R)-dihydroquercetin and (2S,3S)-dihydroquercetin)) was purchased from Bionet, and optically-active dihydroquercetin ((2R,3R)-dihydroquercetin) was purchased from SIGMA.

2) Preparation of Test Substances

Metformin was dissolved in 10% FBS-RPMI1640 medium to prepare 200 mmol/L metformin (final concentration 20 mmol/L). Dihydroquercetin was dissolved in ethanol, and diluted with medium to prepare 10 mmol/L dihydroquercetin (final concentration 1 mmol/L).

3) Cell

Human lung fibroblast-derived cell line WI-38 was obtained from ATCC (catalog no. CCL-75, Exp. Cell. Res., 25: 585-621, 1961). The cells were cultured in. 10% FBS-RPMI1640 medium under the conditions of 37° C., 5% $CO_2$.

4) Addition of Test Substances and Measurement

On the following day after cell seeding, dihydroquercetin was added and the cells were cultured for 1 hr. Then, metformin was added and the cells were cultured for 6 hr. The conditioned medium was sampled, and the concentration of the lactate contained in the medium was measured and evaluated. Each group (N=3) was treated as follows:
(1) Control (vehicle control) group: 1% ethanol containing medium
(2) Dihydroquercetin single-treated group: dihydroquercetin 1 mmol/L
(3) Metformin single-treated group: metformin 20 mmol/L
(4) Combined-treated group: metformin 20 mmol/L+dihydroquercetin 1 mmol/L The passage-cultured WI-38 cells were dissociated with trypsin, and suspended in fresh medium. The cell density of the cell suspension was determined using a hematocytometer and adjusted to $2.5 \times 10^5$ cells/mL. The cells were seeded on 24-well multiwell culture plate (IWAKI) at 0.5 mL per well, and cultured overnight under the conditions of 37° C., 5% $CO_2$. Thereto was added a medium containing a given concentration of dihydroquercetin and the cells were cultured for 1 hr, a medium containing a given concentration of metformin was added and the cells were further cultured for 6 hr. After culture, the culture supernatant from each well was sampled and passed through a filter for molecular weight cut-off 10 kDa to obtain the filtrate. Using the Lactate Assay Kit II (BioVision) catalog no. K627-100, lactate concentration was measured. The cells after sampling of the culture supernatant were washed twice with D-PBS, and cell lysis buffer was added to prepare whole cell lysates. The concentrations of the protein in the whole cell lysates were measured using BCA protein assay, and the lactate concentration of each well was normalized with the protein concentration.

5) Statistical Analysis

The results are shown in mean value (MEAN)±standard deviation (SD).

To evaluate the influence of dihydroquercetin on the metformin-induced produced lactate content, the Student's t-test was performed for the concentration of lactate in the medium between the control group and the dihydroquercetin single agent treated group, and between the control group and the metformin single agent treated group. In addition, to evaluate an influence of the combination of dihydroquercetin and metformin for normalized produced lactate content, a two-way ANOVA (two-tailed) (factors: group and concentration) was performed between the dihydroquercetin single agent treated group (groups 1 and 2) and the metformin treated group (groups 3 and 4). When normalized produced lactate content in the dihydroquercetin single agent treated group is significant compared to that in the control group, the agent was judged to have a suppressive action on lactate production. When normalized produced lactate content in the metformin single agent treated group is significant compared to that in the control group, the agent was judged to have an inducing action on lactate production. When the difference in normalized produced lactate content between combined-treated group and metformin single agent treated group was significantly larger than that between the control group and dihydroquercetin single agent treated group, dihydroquercetin was defined as having a suppressive effect on the content. The analysis was performed using SAS software Release 9.3 (SAS Institute Japan). The differences were considered statistically significant when the p value was less than 0.05.

6) Results

Figure 4:
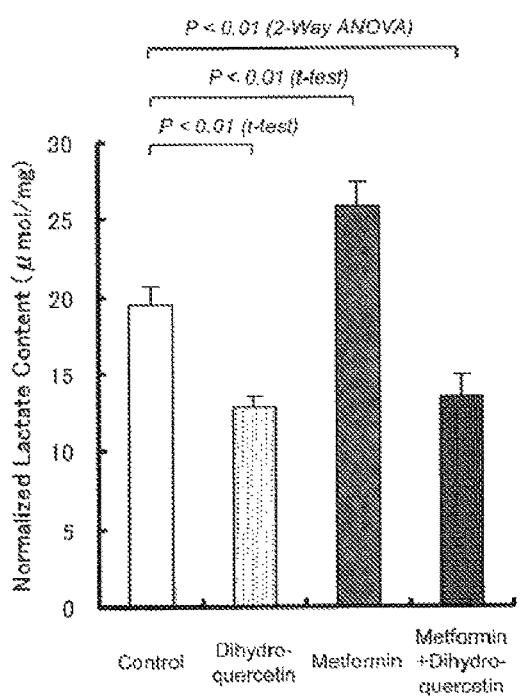
FIG. 4 shows the results of racemate of dihydroquercetin ((2R,3R)-dihydroquercetin and (2S,3S)-dihydroquercetin) in Example 10.
Figure 5:
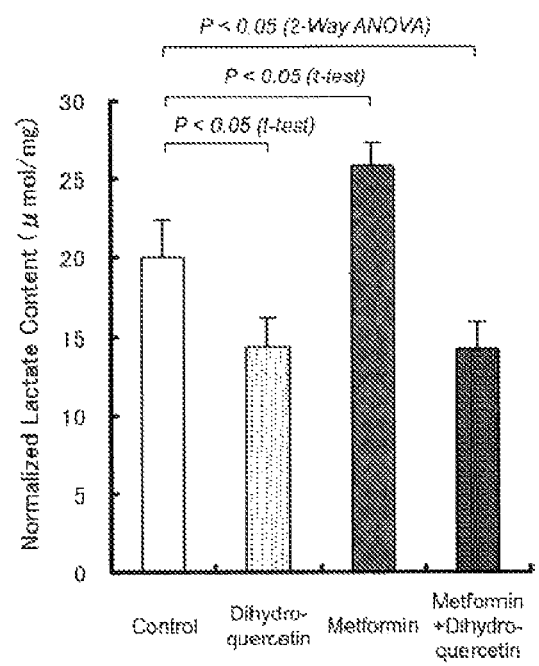
FIG. 5 shows the results of optically-active dihydroquercetin ((2R,3R)-dihydroquercetin) in Example 10.

Both the racemate and optically-active dihydroquercetin suppressed lactate production in WI-38 as compared with the control group. Metformin induced lactate production in the cells and this was significantly suppressed by both the racemate and optically-active dihydroquercetin (Racemate; FIG. 4, Optically-active; FIG. 5).

7) Conclusion

In WT-38 cells, a suppressive effect of dihydroquercetin on metformin-induced lactate production by the racemate and optically-active dihydroquercetin was observed. This indicated a clinical usefulness of dihydroquercetin in reducing the risk of lactic acidosis caused by metformin administration.

[Example 11] The Suppressive Effect on Cancer Cell Proliferation-Related Signal Pathway by Dihydroquercetin Single Agent in a Human Pancreatic Cancer Cell Line AsPC-1 (In Vitro)

1) Test Substances

Dihydroquercetin (racemate of (2R,3R)-dihydroquercetin and (2S,3S)-dihydroquercetin) was purchased from Bionet.

2) Preparation of Test Substances

Dihydroquercetin was dissolved in ethanol, and diluted with medium to prepare 5 and 10 mmol/L dihydroquercetin (final concentration 0.5 and 1 mmol/L).

3) Cell

The human pancreatic cancer-derived cell line AsPC-1 was obtained from Dainippon Pharmaceutical Co., Ltd. (now DS PHARMA BIOMEDICAL CO., LTD., In Vitro. 1982; 18: 24-34). The cells were cultured in 10% FBS-RPMI1640 medium under the conditions of 37° C., 5% $CO_2$.

4) Addition of Test Substances and Measurement

On the following day after cell seeding, test substances were added and the cells were cultured for 6 hr before harvesting them. The amounts of relative phospho-4E-BP1 protein contained in the prepared whole cell lysates were measured and evaluated. Each group (N=3) was treated as follows:
(1) Control (vehicle control) group: 1% ethanol containing medium
(2) Dihydroquercetin single-treated group: dihydroquercetin 0.5 mmol/L
(3) Dihydroquercetin single-treated group: dihydroquercetin 1 mmol/L The passage-cultured AsPC-1 cells were dissociated with trypsin, and suspended in fresh medium. The cell density of the cell suspension was determined using a hematocytometer and adjusted to $1 \times 10^6$ cells/mL. The cells were seeded on 12-well multiwell culture plate at 0.5 mL per well, and cultured overnight under the conditions of 37° C., 5% $CO_2$. On the following day, medium containing dihydroquercetin, at the given concentration, was added into each well. After incubation for 6 hr, the cells in each well were washed twice with D-PBS, and whole cell lysates were prepared using cell lysis buffer. Upon centrifugation, the supernatant was sampled, and the amounts of relative phospho-4E-BP1 (Thr37/Thr46) protein in the samples were quantified using ELISA kits in the same manner as in Example 1. The concentrations of the total protein in the whole cell lysates were measured using BCA protein assay, and the relative phospho-4E-BP1 protein amount of each well was normalized with the total protein amount.

5) Statistical Analysis

The results are shown in mean value (MEAN)±standard deviation (SD).

To evaluate the dose dependency of dihydroquercetin on the relative phospho-4E-BP1 protein amount, the linear regression analysis was performed. As a result, dose dependency was observed. Then, the Williams' test (one-tailed) was performed between the control group and the single agent treated group. As a result, a significant suppressive action of dihydroquercetin at not less than 0.5 mmol/L on relative phospho-4E-BP1 protein amount was observed. When relative phospho-4E-BP1 protein amount in the dihydroquercetin single agent-treated group is significant compared to that in the control group, the agent was judged to have a suppressive action on the amount. The analysis was performed using SAS software Release 9.3 (SAS Institute Japan). The differences were considered statistically significant when the p value was less than 0.05.

6) Results

Figure 6:
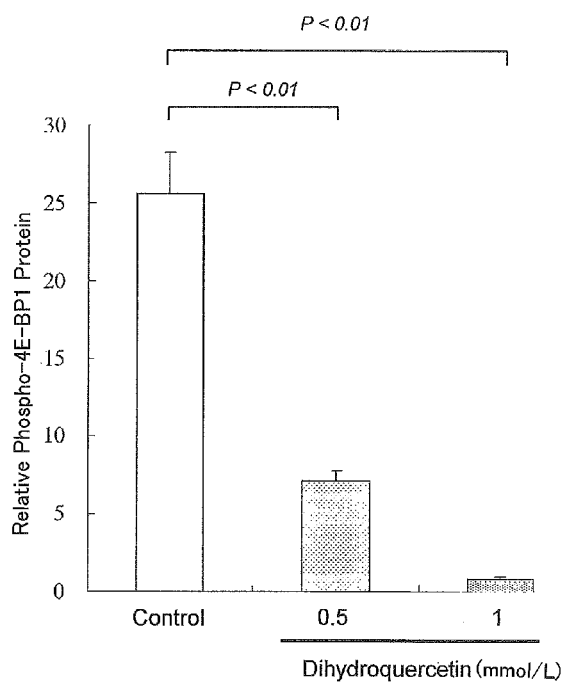
FIG. 6 shows the results of Example 11.

Dihydroquercetin showed a dose-dependent suppressive effect on the relative phospho-4E-BP1 protein amount (FIG. 6).

7) Conclusion

In AsPC-1 cells, a dose-dependent suppressive effect on proliferation-related signal pathway by the dihydroquercetin single agent was observed. This indicated the usefulness of dihydroquercetin in cancer chemotherapy.

[Example 12] The Suppressive Effect on Surface Marker Expression of Cancer Stem Cells by Combined Use of Metformin and Dihydroquercetin in a Human Pancreatic Cancer Cell Line AsPC-1 (In Vitro)

1) Test Substances

Metformin was purchased from Wako Pure Chemical Industries, Ltd. Dihydroquercetin (racemate of (2R,3R)-dihydroquercetin and (2S,3S)-dihydroquercetin) was purchased from Bionet. Gemcitabine was purchased from Toronto Research. Chemicals Inc.

2) Preparation of Test Substances

Metformin was dissolved in distilled water, and diluted with 10% FBS-RPMI1640 medium to prepare 15 mmol/L metformin. Dihydroquercetin was dissolved in ethanol, and diluted with medium to prepare 0.3 mmol/L dihydroquercetin. Gemcitabine was dissolved in dimethyl sulfoxide (DMSO), and diluted with medium to prepare 100 nmol/L gemcitabine.

3) Cell

Human pancreatic cancer-derived cell line AsPC-1 was obtained from DS PHARMA BIOMEDICAL CO., LTD. The cells were cultured in 10% FBS-RPMI1640 medium under the conditions of 37° C., 5% $CO_2$.

4) Addition of Test Substances and Measurement

Each group (N=10) was treated as follows:
(1) Control (vehicle control) group: 1.5% distilled water, 0.3% ethanol and 0.1% DMSO containing medium
(2) Metformin single-treated group: metformin 15 mmol/L
(3) Dihydroquercetin single-treated group: dihydroquercetin 0.3 mmol/L
(4) Metformin-dihydroquercetin combined-treated group: metformin 15 mmol/L+dihydroquercetin 0.3 mmol/L
(5) Gemcitabine single-treated group: gemcitabine 100 nmol/L
(6) Metformin.dihydroquercetin.gemcitabine combined-treated group: metformin 15 mmol/L+dihydroquercetin 0.3 mmol/L+gemcitabine 100 nmol/L The passage-cultured AsPC-1 cells were dissociated with trypsin, and suspended in fresh medium. The cell density of the cell suspension was determined using a hematocytometer and adjusted to $2\times10^4$ cells/mL. The cells were seeded on 6-well multiwell culture plate (IWAKI) at 3 mL per well, and cultured overnight under the conditions of 37° C., 5% $CO_2$. On the following day, the medium was changed with a medium containing each test substance at the given concentration, and the cells were cultured for 72 hr. The end of the culture, the cells were dissociated with trypsin, and suspended in fresh medium. After washing with FACS (fluorescence activated cell sorting) buffer, the cells were stained with FITC-labeled anti-human CD44 antibody and APC-labeled anti-human CD24 antibody, and treated at 4° C. for 30 min. Thereafter, the cells were washed with the FACS buffer, passed through a 40 micron mesh filter, and the proportion of CD44 and CD24 double positive cells was determined using the flow cytometer (Nippon Becton Dickinson and Company, Ltd.).

5) Statistical Analyses

The results are shown in mean value (MEAN)±standard deviation (SD).

To evaluate the influence of metformin and dihydroquercetin single-treated group and a combined use group on the proportion of CD44 and CD24 double positive cells, unpaired two-way ANOVA was performed to compare the control group with each substance single-treated group and combined-treated group. To evaluate the influence of the gemcitabine single-treated group on the proportion of CD44 and CD24 double positive cells, student's t-test was performed to compare the control group with the gemcitabine single-treated group. In addition, to evaluate the influence of the gemcitabine, metformin and dihydroquercetin combined-treated group on the proportion of CD44 and CD24 double positive cells against the gemcitabine single-treated group, Student's t-test was performed to compare the gemcitabine single-treated group and the gemcitabine, metformin and dihydroquercetin combined-treated group. The analysis was performed using SAS software Release 9.3 (SAS Institute Japan). The differences were considered statistically significant when the p value was less than 0.05.

6) Results

Figure 7:
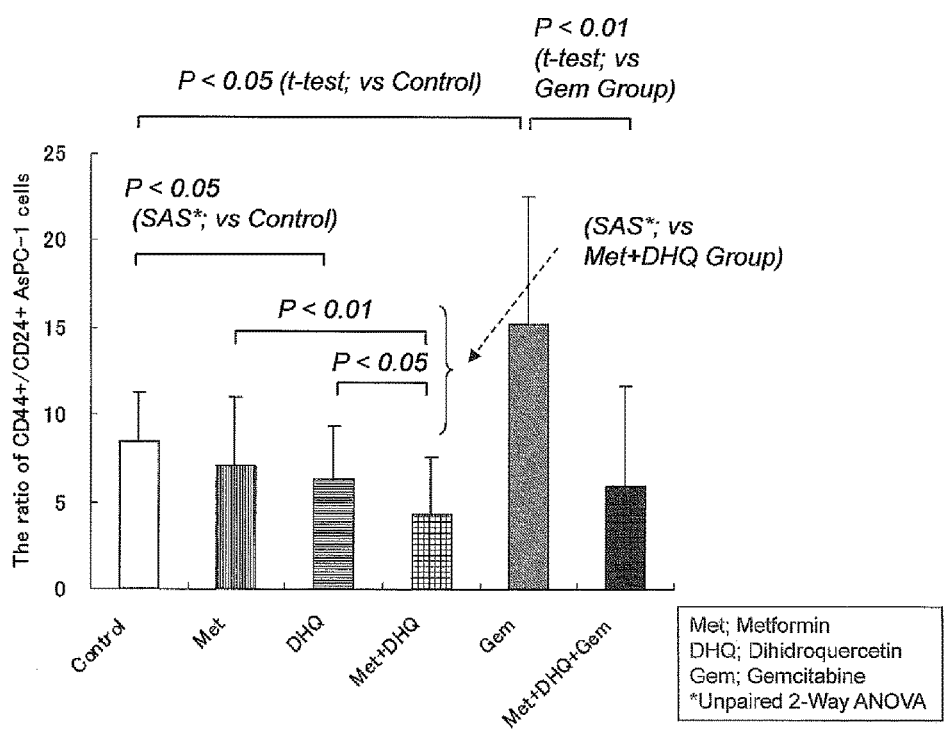
FIG. 7 shows the results of Example 12. In the Figure, Met means metformin, DHQ means dihydroquercetin, and Gem means gemcitabine.

The dihydroquercetin single-treated group and the metformin and dihydroquercetin combined-treated group significantly decreased the proportion of CD44 and CD24 double positive cells in AsPC-1 cells, as compared with the control group. Gemcitabine single-treated group significantly increased the proportion of CD44 and CD24 double positive cells in AsPC-1 cells, as compared with the control group. The increased proportion of CD44 and CD24 double positive cells by gemcitabine single addition was significantly suppressed by the supplemental addition of metformin and dihydroquercetin (FIG. 7).

7) Conclusion

After evaluating the proportion of CD24 and CD44 double positive cells, determined as the cancer stem cells in pancreatic cancer, on pancreatic cancer cell line AsPC-1, the significant decrease were observed by the dihydroquercetin single addition and the combined addition of metformin and dihydroquercetin was observed. On the contrary, the significant increase in the proportion of the double positive cells by gemcitabine was observed. In addition, the above-mentioned increase of the CD24 and CD44 double positive cells by gemcitabine single addition was significantly decreased by the combined addition of metformin and dihydroquercetin. These results suggest that clinical problems, the increase of recurrence risk depending on enrichment of cancer stem cells associated with gemcitabine treatment, may be solved by the combined use of gemcitabine and dihydroquercetin or the combined use of gemcitabine, metformin and dihydroquercetin.

INDUSTRIAL APPLICABILITY

According to the present invention, a medicament having a synergistic anti-malignant tumor effect and reduced side effects, which is useful as an anti-malignant tumor drug, can be provided by combining metformin or a pharmaceutically acceptable salt thereof and dihydroquercetin or a pharmaceutically acceptable salt thereof.

This application is based on a patent application No. 2013-110278 filed in Japan, the contents of which are incorporated in full herein.

The invention claimed is:

1. A method enhancing an anti-malignant tumor action of metformin or a pharmaceutically acceptable salt thereof, comprising administering to a patient with a malignant tumor dihydroquercetin or a pharmaceutically acceptable salt thereof,
   wherein the malignant tumor is lung cancer, liver cancer, bile duct cancer, pancreatic cancer, prostate cancer, breast cancer, or ovarian cancer.

2. A method of enhancing an anti-malignant tumor action, comprising administering to a patient with a malignant tumor dihydroquercetin or a pharmaceutically acceptable salt thereof, in combination with metformin or a pharmaceutically acceptable salt thereof,
   wherein the malignant tumor is lung cancer, liver cancer, bile duct cancer, pancreatic cancer, prostate cancer, breast cancer, or ovarian cancer.

* * * * *